United States Patent [19]

Cain

[11] 4,426,385

[45] Jan. 17, 1984

[54] INSECTICIDAL BICYCLOOXYPHENYL UREAS

[75] Inventor: Paul A. Cain, Dunbar, W. Va.

[73] Assignee: Union Carbide Corporation, Danbury, Conn.

[21] Appl. No.: 305,951

[22] Filed: Sep. 28, 1981

Related U.S. Application Data

[63] Continuation-in-part of Ser. No. 197,595, Oct. 16, 1980, abandoned.

[51] Int. Cl.³ .................. C07C 127/22; C07D 221/00; C07D 307/83; A01N 9/20
[52] U.S. Cl. .................................. 424/263; 546/323; 549/15; 549/23; 549/32; 549/33; 549/52; 549/362; 549/365; 549/408; 549/438; 549/462; 424/250; 424/275; 424/278; 424/283; 424/285; 424/304; 424/309; 424/311; 424/322; 564/44; 560/28; 560/163; 260/465 D; 544/224; 544/238; 544/242; 544/336; 546/268; 546/269; 546/270; 546/286; 546/316

[58] Field of Search ................ 564/44; 424/322, 304, 424/263, 275, 278, 283, 285, 250, 309, 311; 260/465 D; 549/15, 23, 32, 33, 52, 362, 365, 408, 438, 462; 544/224, 238, 242, 336; 546/268, 269, 270, 286, 316, 323; 560/28, 163

[56] References Cited

U.S. PATENT DOCUMENTS

| | | | |
|---|---|---|---|
| 3,748,356 | 7/1973 | Wellinga et al. | 260/553 E |
| 3,989,842 | 11/1976 | Wellinga et al. | 424/322 |
| 3,992,553 | 11/1976 | Sirrenberg et al. | 424/304 |
| 3,993,908 | 1/1976 | Wellinga et al. | 260/553 E |
| 4,041,177 | 8/1977 | Sirrenberg et al. | 424/322 |
| 4,148,902 | 4/1979 | Rigterink | 424/266 |
| 4,275,077 | 6/1981 | Becher et al. | 424/322 |

*Primary Examiner*—Thomas A. Waltz
*Attorney, Agent, or Firm*—R. C. Brown; J. A. Shedden; W. R. Moran

[57] ABSTRACT

Novel bicyclooxyphenyl ureas, such as 1-(bicyclooxyphenyl)-benzoyl ureas, are provided which exhibit pesticidal activity. The compositions are conveniently prepared by reacting an isocyanate with either an amide or a bicyclooxyaniline.

84 Claims, No Drawings

INSECTICIDAL BICYCLOOXYPHENYL UREAS

This application is a continuation-in-part of United States patent application Ser. No. 197,595 filed Oct. 16, 1980 now abandoned.

FIELD OF THE INVENTION

This invention relates in general to novel bicyclooxyphenyl ureas. In one aspect, this invention relates to processes for the preparation of the bicyclooxyphenyl ureas. In a further aspect, the invention relates to pesticidal formulations containing the ureas as at least one of the active ingredients of such compositions. In a still further aspect, the invention is directed to the use of the compositions in controlling plant pests.

DESCRIPTION OF THE PRIOR ART

Prior to the present invention few benzoyl ureas had been reported in the patent literature as having pesticidal activity. For example, U.S. Pat. No. 3,992,553 which issued on Nov. 16, 1976, and U.S. Pat. No. 4,041,177 which issued on Aug. 9, 1977, both disclosed certain benzoylureido-diphenyl ethers which were indicated to possess insecticidal properties. Similarly, U.S. Pat. Nos. 3,748,356 and 3,933,908 also disclosed certain substituted benzoyl ureas and stated that the compositions had strong insecticidal activity. U.S. Pat. No. 4,148,902 which issued Apr. 10, 1979 discloses substituted ((phenylamino)carbonyl) pyridine carboxamides and claims a method of controlling insects in addition to the compositions themselves. However, prior to the present invention no bicyclooxyphenyl ureas, such as, bicyclooxyphenyl benzoyl ureas have been reported in the literature as being useful for the control of plant pests.

DESCRIPTION OF THE INVENTION

The bicyclooxyphenyl ureas of this invention can be conveniently represented by the following formula:

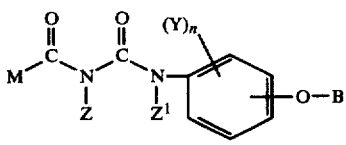

wherein M represents an monocyclic aromatic ring system or a monocyclic heterocyclic ring system containing up to 2 nitrogen atoms, and wherein the rings can contain up to four X substituents wherein each X individually can be halogen, nitro, cyano, or alkyl, polyhaloalkyl, alkoxy or polyhaloalkoxy of from 1 to 3 carbon atoms;

Z and $Z^1$ individually are hydrogen or alkyl of from 1 to 8 carbon atoms, or alkyl of from 1 to 8 carbon atoms which is substituted with at least one of halogen, hydroxyl or alkoxy;

Y individually represents halogen, or alkyl, polyhaloalkyl, alkoxy or polyhaloalkoxy of from 1 to 3 carbon atoms, and n has a value of from 0 to 4;

B is a bicyclic fused ring system which is attached to the oxygen through a carbocyclic ring and wherein (a) at least one ring is a six-membered, unsaturated carbocyclic ring which can contain up to two R and $R^1$ substituents wherein R and $R^1$ can be halogen, nitro, cyano, amino, formamido, formamidino, phenylsulfenyl, phenylsulfinyl, phenylsulfonyl, phenylsulfamido, wherein the phenyl ring optionally may be substituted with one or more halogen, nitro, or alkyl, polyhaloalkyl, alkoxy or polyhaloalkoxy of from 1 to 3 carbon atoms, or R and $R^1$ individually are alkyl, alkoxy, polyhaloalkyl, polyhaloalkoxy, alkenyloxy, polyhaloalkenyloxy, alkynyloxy, polyhaloalkynyloxy, alkylsulfenyl, polyhaloalkylsulfenyl, alkylsulfinyl, polyhaloalkylsulfinyl, alkylsulfonyl, polyhaloalkylsulfonyl, mono- or di-alkylsulfamido, mono- or di-alkylamino, alkylcarbonylamino, alkoxycarbonylamino, mono- or di-alkylaminocarbonyloxy of up to 6 carbon atoms and (b) the second ring, hereinafter also referred to as A, when it is not a five or six-membered carbocyclic can be a five or six-membered saturated or unsaturated heterocyclic ring which can contain in any combination carbonyl or one or two oxygen or sulfur, and up to two $R^2$ and $R^3$ substituents attached to unsaturated ring carbon atoms wherein $R^2$ and $R^3$ individually can be halogen, nitro, cyano, or alkyl, polyhaloalkyl, alkoxy, polyhaloalkoxy, alkylthio, arylthio, alkylsulfinyl, arylsulfinyl, alkylsulfonyl, arylsulfonyl, alkylsulfamido, arylsulfamido, alkoxycarbonylamino, or alkylcarbonylamino of from 1 to 6 carbon atoms, or the ring can contain up to two $R^4$ and $R^5$ substituents attached to saturated ring carbon atoms wherein $R^4$ and $R^5$ individually can be alkyl or polyhaloalkyl of from 1 to 6 carbon atoms; with the proviso that when B is a naphthyl group attached through an oxygen to the number 4 carbon atom of the phenyl group, then (a) if X is halogen and is mono or disubstituted in the ortho position of a benzoyl ring (b) if Z, $Z^1$, $R^2$ and $R^3$ are hydrogen and (c) if Y represents a halogen substituted at the number three carbon atom of the phenyl ring, or if such carbon atom contains only hydrogen then R and $R^1$ can not both be hydrogen or halogen or a combination of hydrogen and halogen.

A preferred class of bicyclooxyphenyl ureas coming within the above generic formula can be represented by:

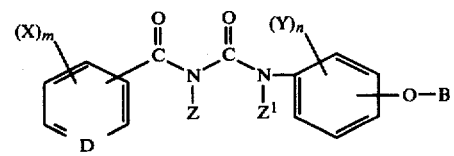

wherein D is nitrogen or carbon and X, Z, Y, B, $Z^1$ and n are as previously indicated, and m has a value of from zero to four with the same proviso pertaining to X, and Y and B as herebefore indicated.

The B moiety of the above formula is a bicyclic fused ring system which can be attached to the linking oxygen atom through a carbocyclic ring. Hence, particularly preferred compositions are those presented by the following formula:

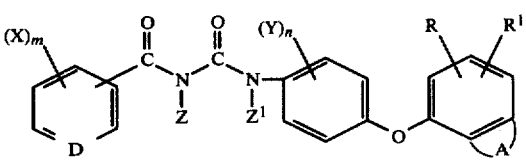

wherein the substituents are as previously indicated.

Illustrative of the B moieties which are linked to the phenyl group through oxygen are the following:

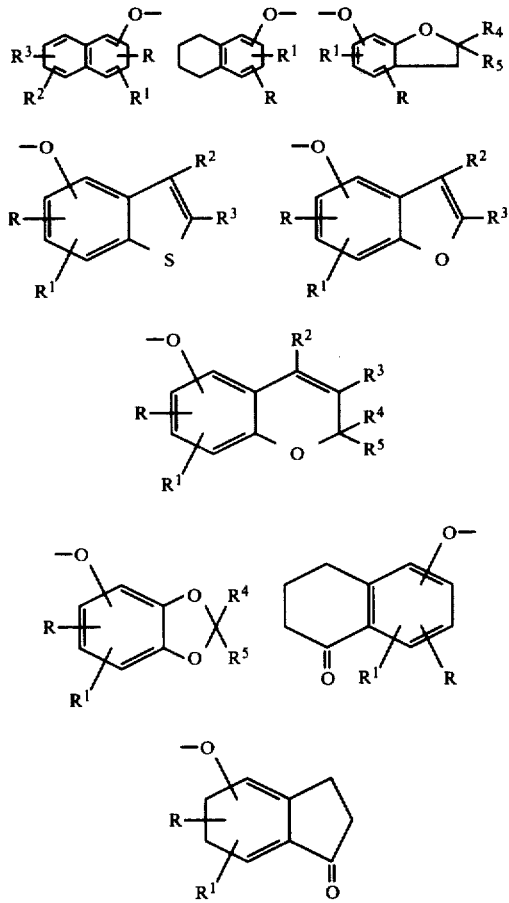

wherein the substituents are as previously defined.

It is readily apparent that preceding formulae encompass a wide variety of novel ureas and include but are not limited to compositions such as the following:

1-(3,5-dichloro-4-[4-nitro-1-naphthoxy]phenyl)-3-(2-chlorobenzoyl)urea.
1-(3,5-dichloro-4-[4-nitro-1-naphthoxy]phenyl)-3-(2,6-dichlorobenzoyl)urea.
1-(3,5-dichloro-4-[4-nitro-1-naphthoxy]phenyl)-3-(2,6-difluorobenzoyl)urea.
1-(3,5-dichloro-4-[4-nitro-1-naphthoxy]phenyl)-3-(2-chloro-6-fluorobenzoyl)urea.
1-(3,5-dichloro-4-[4-cyano-1-naphthoxy]phenyl)-3-(2-chlorobenzoyl)urea.
1-(3,5-dichloro-4-[4-cyano-1-naphthoxy]phenyl)-3-(2,6-dichlorobenzoyl)urea.
1-(3,5-dichloro-4-[4-cyano-1-naphthoxy]phenyl)-3-(2,6-difluorobenzoyl)urea.
1-(3,5-dichloro-4-[4-cyano-1-naphthoxy]phenyl)-3-(2-chloro-6-fluorobenzoyl)urea.
1-(3,5-dichloro-4-[4-trifluoromethyl-1-naphthoxy]phenyl)-3-(2-chlorobenzoyl)urea.
1-(3,5-dichloro-4-[4-trifluoromethyl-1-naphthoxy]phenyl)-3-(2,6-dichlorobenzoyl)urea.
1-(3,5-dichloro-4-[4-trifluoromethyl-1-naphthoxy]phenyl)-3-(2,6-difluorobenzoyl)urea.
1-(3,5-dichloro-4-[4-trifluoromethyl-1-naphthoxy]phenyl)-3-(2-chloro-6-fluorobenzoyl)urea.
1-(4-[1-napthoxy]-3-trifluoromethylphenyl)-3-(2,6-dimethoxybenzoyl)urea.
1-(3,5-dichloro-4-[4-chloro-2,2-dimethyl-2,3-dihydro-7-benzofuranyloxy]phenyl)-3-(2-chlorobenzoyl)urea.
1-(3,5-dichloro-4-[2,2-dimethyl-2,3-dihydro-4-nitro-7-benzofuranyloxy]phenyl)-3-(2,6-dichlorobenzoyl)urea.
1-(3,5-dichloro-4-[4-cyano-2,2-dimethyl-2,3-dihydro-7-benzofuranyloxy]phenyl)-3-(2,6-difluorobenzoyl)urea.
1-(3,5-dichloro-4-[2,2-dimethyl-2,3-dihydro-4-trifluoromethyl-7-benzofuranyloxy]phenyl-3-(2-chloro-6-fluorobenzoyl)urea.
1-(3,5-dibromo-4-[2,3-dihydro-2,2-dimethyl-7-benzofuranyloxy]phenyl)-3-(2,6-dimethoxybenzoyl)urea.
1-(3,5-dichloro-4-[5,6,7,8-tetrahydro-4-trifluoromethyl-1-naphthoxy]-phenyl)-3-(2,6-dichlorobenzoyl)urea.
1-(3,5-dichloro-4-[4-chloro-5,6,7,8-tetrahydro-1-naphthoxy]phenyl)-3-(2,6-difluorobenzoyl)urea.
1-(3,5-dichloro-4-[4-nitro-4,6,7,8-tetrahydro-1-naphthoxy]phenyl)-3-(2-chloro-6-fluorobenzoyl)urea.
1-(3,5-dichloro-4-[4-cyano-5,6,7,8-tetrahydro-1-naphthoxy]-3-(2-chlorobenzoyl)urea.
1-(3-chloro-4-[2,4-dichloro-5,6,7,8-tetrahydro-1-naphthoxy]-3-(2,6-dimethoxybenzoyl)urea.
1-(3-bromo-4-[3-bromo-7-benzofuranyloxy]-5-methylphenyl)-3-benzoylurea.
1-(3-chloro-4-[2-chloro-4-phenylsulfenyl-6-benzofuranyloxy]-5-ethylphenyl)-3-(2,6-diisopropylbenzoyl)urea.
1-(3,5-dimethoxy-4-[3-fluoro-4-benzofuranyloxy]-3-(2-trifluoromethoxybenzoyl)urea.
1-(4-[7-{2,4-dichlorophenylsulfenyl}-3-isopropoxy-5-benzofuranyloxy]phenyl)-3-(2-ethoxybenzoyl)urea.
1-(3-iodo-4-[4-methylsulfenyl-7-benzothienyloxy]phenyl)-3-(2-chloro-6-fluorobenzoyl)urea.
1-(3,5-difluoro-4-[7-fluoro-4-trifluoromethyl-6-benzothienyloxy]phenyl)-3-(2-difluoromethylbenzoyl)urea.
1-(4-[6,7-dichloro-3-nitro-4-benzothienyloxy]-3-heptafluoropropoxyphenyl)-3-(2,6-dibromobenzoyl)urea.
1-(3,5-dichloro-4-[4-benzothienyloxy]phenyl)-1-(2-chloro-6-fluorobenzoyl)urea.
1-(3,5-dichloro-4-[7-chloro-4-benzothienyloxy]phenyl-1-(2,6-difluorobenzoyl)urea.
1-(3-chloro-4-[7-chloro-4-benzothienyloxy]phenyl-1-(2,6-dimethoxybenzoyl)urea.
1-(4-[6-bromo-4-chloro-2,3-difluoro-5-benzothienyloxy]-3-isopropoxyphenyl)-3-(2-bromobenzoyl)urea.
1-(4-{5-fluoro-4-benzodioxyalanyloxy]-3-isopropylphenyl)-3-(2,6-bistrifluoromethylbenzoyl)urea.
1-(3,5-dichloro-4-[benzodioxalanyloxy]phenyl)-3-(2,6-difluorobenzoyl)urea.
1-(4-[2,2-bistrifluoromethyl-5-benzodioxalanyloxy]-3,5-dichlorophenyl)-3-(2-chloro-6-fluorobenzoyl)urea.
1-(3-chloro-5-n-pentyl-4-[2-trifluoromethyl-7-trifluoromethylsulfinyl-4-benzodioxalanyloxy]-phenyl)-3-(2,6-dichlorobenzoyl)urea.
1-(3-perfluoroisopropyl-4-[2,2,6-trimethyl-4-benzodioxalanyloxy]phenyl)-3-(2-iodobenzoylurea).
1-(4-[6-bromo-2-n-pentyl-5-benzodioxalanyloxy]-3-difluoromethylphenyl)-3-(2,6-diiodobenzoyl)urea.

1-(4-[4-benzodioxalanyloxy]-3,5-dichlorophenyl)-3-(2,6-difluorobenzoyl)urea.
1-(4-[7-chloro-4-benzodioxalanyloxy]-3,5-dichlorophenyl)-3-(2-chloro-6-fluorobenzoyl)urea.
1-(4-[4-benzodioxalanyloxy]-3-chlorophenyl)-3-(2,6-dimethoxybenzoyl)urea.
1-(3,5-dichloro-4-[5-oxo-5,6,7,8-tetrahydro-1-naphthoxy]phenyl-3-(2,6-difluorobenzoyl)urea.
1-(3-chloro-4-[2,4-dichloro-5-oxo-5,6,7,8-tetrahydro-1-naphthoxy]phenyl)-3-(2-chloro-6-fluorobenzoyl)urea.
1-(4-[4-nitro-5-oxo-5,6,7,8-tetrahydro-1-naphthoxy]-3-trifluoromethylphenyl)-3-(2-chlorobenzoyl)urea.
1-(4-[2-chloro-4-nitro-5-oxo-5,6,7,8-tetrahydro-1-naphthoxy]3,5-dibromophenyl)-3-(2,6-dichlorobenzoyl)urea.
1-(3-chloro-4-[2-chloro-4-ethylsulfenyl-1-naphthoxy]phenyl)-3-(2-chlorobenzoyl)urea.
1-(3-chlorodifluoromethyl-4-[5,8-dichloro-4-trichloromethylsulfenyl-1-naphthoxy]phenyl)-3-(2-chlorobenzoyl)urea.
1-(3,5-dichloro-4-[4-methylsulfinyl-5,6,7,8-tetrahydro-1-naphthoxy]phenyl)-3-(2,6-dichlorobenzoyl)urea.
1-(3,5-dichloro-4-[4-benzofuranyloxy]phenyl)-1-(2,6-difluorobenzoyl)urea.
1-(3-chloro-4-[7-chloro-4-benzofuranyloxy]phenyl-1-(2-chloro-6-fluorobenzoyl)urea.
1-(4-[7-chloro-4-benzofuranyloxy]-3,5-dichlorophenyl)-3-(2-chlorobenzoyl)urea.
1-(4-[4-benzofuranyloxy]-3-chlorophenyl)-3-(2,6-dimethoxybenzoyl)urea.
1-(4-[-tert-butyl-1-naphthoxy]-3-bromodifluoromethylphenyl)-3-(2,6-difluorobenzoyl)urea.
1-(3-bromo-5-chloro-4-[4-isopropylsulfamido-1-naphthoxy]phenyl)-3-(2-chloro-6-fluorobenzoyl)urea.
1-(3-dibromomethyl-4-[4-phenylsulfenyl-1-naphthoxy]phenyl)-3-(2,6-dibromobenzoyl)urea.
1-(3,5-difluoro-4-[4-phenylsulfinyl-1-naphthoxy]phenyl)-3-(2,6-difluorobenzoyl)urea.
1-(3-dichloromethyl-4-[4-phenylsulfonyl-1-naphthoxy]phenyl)-3-3-(2-trifluoromethylbenzoyl)urea.
1-(4-[4-phenylsulfamido-5,6,7,8-tetrahydro-1-naphthoxy]-3-trifluoromethylphenyl)-3-(2-methoxybenzoyl)urea.
1-(4[4-{N-ethyl-N-phenylsulfamido}-5,6,7,8-tetrahydro-1-naphthoxy]-3-iodophenyl)-3-(2-trifluoromethoxybenzoyl)urea.
1-(3-chloro-4-[4-{4-chloro-3-methylphenylsulfenyl}-5,6,7,8-tetrahydro-1-naphthoxy]phenyl)-1-(2-methoxy-6-methylbenzoyl)urea.
1-(3,5-diiodo-4-[4-{2-nitro-4-trifluoromethylsulfinyl}-1-naphthoxy]phenyl)-3-(2-trichloromethylbenzoyl)urea.
1-(3,5-dibromo-4-[4-{3-chloro-4-trifluoromethylsulfonyl}-4,6,7,8-tetrahydro-1-naphthoxy]phenyl)-3-(2,6-dimethylbenzoyl)urea.
1-(4-[4-{N-(4-chlorophenyl)sulfamido}-1-naphthoxy]-3-iodo-5-methylphenyl)-3-(2-trichloromethoxybenzoyl)urea.
1-(4-[4-{N-(4-nitrophenyl)-N-isopropylsulfamido}-5,6,7,8-tetrahydro-1-naphthoxy]phenyl)-3-(2-chloro-6-methylbenzoylurea.
1-(3,5-dichloro-4-[2,3-dihydro-2,2-dimethyl-7-benzofuranyloxy]phenyl)-3-(2,6-difluorobenzoyl)urea.
1-(3,5-dichloro-4-[4-chloro-2,3-dihydro-2,2-dimethyl-7-benzofuranyloxy]phenyl)-3-(2,6-fluorobenzoyl)urea.
1-(3,5-dichloro-4-[2,3-dihydro-2,2-dimethyl-7-benzofuranyloxy]phenyl)-3-(2-chlorobenzoyl)urea.
1-(3,5-dichloro-4-[2,3-dihydro-2,2-dimethyl-7-benzofuranyloxy]phenyl)-2-(2-chloro-6-fluorobenzoyl)urea.
1-(3,5-dichloro-4-[4-chloro-2,3-dihydro-2,2-dimethyl-7-benzofuranyloxy]phenyl)-3-(2-chlorobenzoyl)urea.
1-(3,5-dichloro-4-[4-chloro-2,3-dihydro-2,2-dimethyl-7-benzofuranyloxy]phenyl)-3-(2-chloro-6-fluorobenzoyl)urea.
1-(3,5-dichloro-4-[4-chloro-2,3-dihydro-2,2-dimethyl-7-benzofuranyloxy]phenyl)-3-(2,6-dimethoxybenzoyl)urea.
1-(3,5-dichloro-4-[2,3-dihydro-2,2-dimethyl-7-benzofuranyloxy]phenyl)-3-(2,6-dimethoxybenzoyl)urea.
1-(4-[4-chloro-1-naphthoxy]-3,5-dichlorophenyl)-3-([2,4-dichloro-3-pyridinyl]carbonyl)urea.
1-(4-[4-chloro-1-naphthoxy]-3-trifluoromethylphenyl)-3-([2,4-dimethoxy-3-pyridinyl]carbonyl)urea.
1-(4-[1-naphthoxy]-3-chlorophenyl)-3-([3,5-dichloro-4-pyridinyl]carbonyl)urea.
1-(4-[5,6,7,8-tetrahydro-1-naphthoxy]-3,5-dichlorophenyl)-3-([2,3,5-trichloro-4-pyridinyl]carbonyl)urea.
1-(4-[4-chloro-1-naphthoxy]-3,5-dichlorophenyl)-3-([2,4-difluoro-3-pyridinyl]carbonyl)urea.
1-(4-[4-chloro-1-naphthoxy]-3,5-dichlorophenyl)-3-([3-chloro-2-pyrazinyl]carbonyl)urea.
1-(4-[4-chloro-1-naphthoxy]-3-trifluoromethylphenyl)-3-([3-methoxy-2-pyrazinyl]carbonyl)urea.
1-(4-[2,4-dichloro-1-naphthoxy]-3,5-dichlorophenyl)-3-([3-trifluoromethyl-2-pyrazinyl]carbonyl)urea.
1-(4-[4-chloro-1-naphthoxy]-3,5-dichlorophenyl)-3-([2-fluoro-3-pyrazinyl]carbonyl)urea.
1-(4-[1,6-dichloro-2-naphthoxy]-3,5-dichlorophenyl)-3-([2,4-difluoro-3-pyridinyl]carbonyl)urea.
1-(4-[6-chloro-2-naphthoxy]-3-chlorophenyl)-3-([2-chloro-3-pyridinyl]carbonyl)urea.
1-(4-[1,6-dichloro-2-naphthoxy]-3-chlorophenyl)-3-([3-chloro-2-pyrazinyl]carbonyl)urea.
1-(4-[4-chloro-1-naphthoxy]-3,5-dichlorophenyl)-3-([2-pyrimidinyl]carbonyl)urea.
1-(4-[1,6-dichloro-2-naphthoxy]-3-chloro)-3-([2-pyrimidinyl]carbonyl)urea.
1-(4-[4-chloro-1-naphthoxy]-3,5-dichlorophenyl)-3-([5-chloro-4-pyrimidinyl]carbonyl)urea.
1-(4-[1,6-dibromo-1-naphthoxy]-3-chlorophenyl)-3-([5-methoxy-4-pyrimidinyl]carbonyl)urea.
1-(4-[4-chloro-1-naphthoxy]-3,5-dichlorophenyl)-3-([4,6-dichloro-5-pyrimidinyl]carbonyl)urea.
1-(4-[6-bromo-2-naphthoxy]-3-chlorophenyl)-3-([4,6-dimethoxy-5-pyrimidinyl]carbonyl)urea.
1-(4-[1,6-dibromo-2-naphthoxy]-3-chlorophenyl)-3-([4,6-difluoro-5-pyrimidinyl]carbonyl)urea.
1-(3,5-dichloro-4-[4-methoxy-1-naphthoxy]phenyl)-3-(2,6-difluorobenzoyl)urea.
1-(3,5-dichloro-4-[4-methoxy-1-naphthoxy]pheny)-3-(2-chlorobenzoyl)urea.
1-(3,5-dichloro-4-[4-methoxy-1-naphthoxy]phenyl)-3-(2-chloro-6-fluorobenzoyl)urea.
1-(3-chloro-4-[4-dimethylamino-1-naphthoxy]phenyl)-3-(2,6-difluorobenzoyl)urea.
1-(3-chloro-4-[4-dimethylamino-1-naphthoxy]phenyl)-3-(2-chlorobenzoyl)urea.

1-(3-chloro-4-[4-dimethylamino-1-naphthoxy]-phenyl)-3-(2-chloro-6-fluorobenzoyl)urea.
1-(4-[4-chloro-1-naphthoxy]-3-methylphenyl)-3-(2,6-difluorobenzoyl)urea.
1-(4-[4-chloro-1-naphthoxy]-3-methylphenyl)-3-(2-chlorobenzoyl)urea.
1-(4-[4-chloro-1-naphthoxy]-3-methylphenyl)-3-(2-chloro-6-fluorobenzoyl)urea.
1-(3-chloro-4-[4-chloro-1-naphthoxy]-5-methylphenyl-3-(2,6-difluorobenzyl)urea.
1-(3-chloro-4-[4-chloro-1-naphthoxy]-5-methylphenoyl-3-(2-chlorobenzoyl)urea.
1-(3-chloro-4-[4-chloro-1-naphthoxy]-5-methylphenyl)-3-(2-chloro-6-fluorobenzoyl)urea.
1-(4-[4-chloro-1-naphthoxy]-3,5-dimethylphenyl)-3-(2,6-difluorobenzoyl)urea.
1-(4-[4-chloro-1-naphthoxy]-3,5-dimethylphenyl)-3-(2-chlorobenzoyl)urea.
1-(4-[4-chloro-1-naphthoxy]-3,5-dimethylphenyl)-3-(2-chloro-6-fluorobenzoyl)urea.
1-(3-chloro-4-[4-chloro-1-naphthoxy]-2,5-dimethylphenyl)-3-(2,6-difluorobenzoyl)urea.
1-(3-chloro-4-[4-chloro-1-naphthoxy]-2,5-dimethylphenyl)-3-(2-chlorobenzoyl)urea.
1-(3-chloro-4-[4-chloro-1-naphthoxy]-2,5-dimethylphenyl)-3-(2-chloro-6-fluorobenzoyl)urea.
1-(4-[4-chloro-5,6,7,8-tetrahydro-1-naphthoxy]-3,5-dimethylpheny)-3-(2,6-difluorobenzoyl)urea.
1-(4-[4-chloro-5,6,7,8-tetrahydro-1-naphthoxy]-3,5-dimethylphenyl)-3-(2-chlorobenzoyl)urea.
1-(4-[4-chloro-5,6,7,8-tetrahydro-1-naphthoxy]-3,5-dimethylphenyl)-3-(2-chloro-6-fluorobenzoyl)urea.
1-(3-chloro-4-[4-chloro-5,6,7,8-tetrahydro-1-naphthoxy]-5-methylphenyl)-3-(2,6-difluorobenzoyl)urea.
1-(3-chloro-4-[4-chloro-5,6,7,8-tetrahydro-1-naphthoxy]-5-methylphenyl)-3-(2-chlorobenzoyl)urea.
1-(3-chloro-4-[4-chloro-5,6,7,8-tetrahydro-1-naphthoxy]-5-methylphenyl)-3-(2-chloro-6-fluorobenzoyl)urea.
1-(4-[4-chloro-5,6,7,8-tetrahydro-1-naphthoxy]-3,5-dichlorophenyl)-3-(2,6-difluorobenzoyl)urea.
1-(4-[4-chloro-5,6,7,8-tetrahydro-1-naphthoxy]-3,5-dichlorophenyl)-3-(2-chlorobenzoyl)urea.
1-(4-[4-chloro-5,6,7,8-tetrahydro-1-naphthoxy]-3,5-dichlorophenyl)-3-(2-chloro-6-fluorobenzoyl)urea.
1-(4-[4-chloro-5,6,7,8-tetrahydro-1-naphthoxy]-3-methylphenyl)-3-(2,6-difluorobenzoyl)urea.
1-(4-[4-chloro-5,6,7,8-tetrahydro-1-naphthoxy]-3-methylphenyl)-3-(2-chlorobenzoyl)urea.
1-(4-[4-chloro-5,6,7,8-tetrahydro-1-naphthoxy]-3-methylphenyl)-3-(2-chloro-6-fluorobenzoyl)urea.
1-(3,5-dichloro-4-[4-dimethylamino-5,6,7,8-tetrahydro-1-naphthoxy]phenyl)-3-(2,6-difluorobenzoyl)urea.
1-(3,5-dichloro-4-[4-dimethylamino-5,6,7,8-tetrahydro-1-naphthoxy]phenyl)-3-(2-chlorobenzoyl)urea.
1-(3,5-dichloro-4-[4-dimethylamino-5,6,7,8-tetrahydro-1-naphthoxy]phenyl)-3-(2-chloro-6-fluorobenzoyl)urea.
1-(4-[4-dimethylamino-5,6,7,8-tetrahydro-1-napthoxy]-3-methylphenyl)-3-(2-chloro-6-fluorobenzoyl)urea.
1-(4-[4-dimethylamino-5,6,7,8-tetrahydro-1-naphthoxy]-3-methylphenyl)-3-(2-chlorobenzoyl)urea.
1-(4-[4-dimethylamino-5,6,7,8-tetrahydro-1-naphthoxy]-3-(2,6-difluorobenzoyl)urea.
1-(3-chloro-4-[4-chloro-5,6,7,8-tetrahydro-1-naphthoxy]phenyl)-3-(2,6-difluorobenzoyl)urea.
1-(3-chloro-4-[4-chloro-5,6,7,8-tetrahydro-1-naphthoxy]-3-(2-chlorobenzoyl)urea.
1-(3-chloro-4-[4-chloro-5,6,7,8-tetrahydro-1-naphthoxy]-3-(2-chloro-6-fluorobenzoyl)urea.
1-(4-[4-chloro-5,6,7,8-tetrahydro-1-naphthoxy]-3,5-dimethlphenyl)-3-(2,6-difluorobenzoyl)urea.
1-(4-[4-chloro-5,6,7,8-tetrahydro-1-naphthoxy]-3,5-dimethylphenyl)-3-(2-chlorobenzoyl)urea.
1-(4-[4-chloro-5,6,7,8-tetrahydro-1-naphthoxy]-3,5-dimethlphenyl)-3-(2-chloro-6-fluorobenzoyl)urea.
1-(3-chloro-4-[4-chloro-5,6,7,8-tetrahydro-1-naphthoxy]-5-methylphenyl)-3-(2,6-difluorobenzoyl)urea.
1-(3-chloro-4-[4-chloro-5,6,7,8-tetrahydro-1-naphthoxy]-5-methylphenyl)-3-(2-chloro-6-fluorobenzoyl)urea.
1-(3-chloro-4-[4-chloro-5,6,7,8-tetrahydro-1-naphthoxy]-5-methylphenyl)-3-(2-chlorobenzoyl)urea.
1-(3-chloro-4-[4-dimethylamino-5,6,7,8-tetrahydro-1-naphthoxy]-5-methylphenyl)-3-(2,6-difluorobenzoyl)urea.
1-(3-chloro-4-[4-dimethylamino-5,6,7,8-tetrahydro-1-naphthoxy]-5-methylphenyl)-3-(2-chloro-6-fluorobenzoyl)urea.
1-(3-chloro-4-[4-dimethylamino-5,6,7,8-tetrahydro-1-naphthoxy]-5-methylphenyl)-3-(2-chlorobenzoyl)urea.
1-(3,5-dimethyl-4-[4-dimethylamino-5,6,7,8-tetrahydro-1-naphthoxy]phenyl)-3-(2,6-difluorobenzoyl)urea.
1-(3,5-dimethyl-4-[4-dimethylamino-5,6,7,8-tetrahydro-1-naphthoxy]phenyl)-3-(2-chlorobenzoyl)urea.
1-(3,5-dimethyl-4-[4-dimethylamino-5,6,7,8-tetrahydro-1-naphthoxy]-3-(2-chloro-6-fluorobenzoyl)urea, and the like.

It should be noted that $X^1$, $Y^1$ and $Y^2$ as used throughout the specification and claims, have the same meaning as X and Y as hereinbefore defined. Additionally, X, $X^1$, Y, $Y^1$, $Y^2$ and $R-R^5$ may also be indicated to represent hydrogen as will be evident from many of the preferred sub-generic formulae of this invention.

Additional benzoyl ureas which are encompassed by this invention include those set forth below in Tables A, B, and C wherein each of the substituents of the formula is defined.

TABLE A

| X | $X^1$ | Y | $Y^1$ | $R^1$ | $R^2$ |
|---|---|---|---|---|---|
| Cl | H | Cl | H | H | H |
| Cl | F | Cl | H | H | H |
| F | F | Cl | H | H | H |
| OCH$_3$ | OCH$_3$ | Cl | H | H | H |
| Cl | Cl | Cl | H | H | H |
| Cl | H | Cl | Cl | H | H |
| Cl | F | Cl | Cl | H | H |
| F | F | Cl | Cl | H | H |
| OCH$_3$ | OCH$_3$ | Cl | Cl | H | H |
| Cl | Cl | Cl | Cl | H | H |
| Cl | F | Cl | H | CH$_3$ | H |
| F | F | Cl | Cl | CH$_3$ | H |
| F | F | Cl | H | CH$_3$ | H |

TABLE A-continued

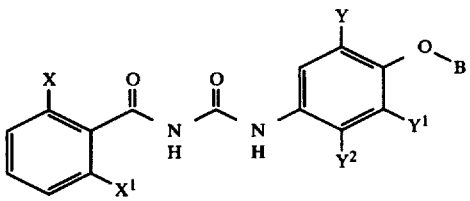

| X | X¹ | Y | Y¹ | R¹ | R² |
|---|---|---|---|---|---|
| OCH₃ | OCH₃ | Cl | Cl | CH₃ | H |
| F | Cl | Cl | H | OCH₃ | H |
| F | Cl | Cl | Cl | OCH₃ | H |
| F | F | Cl | H | OCH₃ | H |
| F | F | Cl | Cl | OCH₃ | H |
| Cl | F | Cl | H | Cl | Cl |
| Cl | F | Cl | Cl | Cl | Cl |
| F | F | Cl | H | Cl | Cl |
| F | F | Cl | Cl | Cl | Cl |

TABLE B

| X | X¹ | Y | Y¹ | Y² | Z² |
|---|---|---|---|---|---|
| F | F | Cl | H | H | CH₃ |
| Cl | H | Cl | H | H | CH₃ |
| F | F | Cl | Cl | H | OC₂H₅ |
| Cl | H | Cl | Cl | H | OC₂H₅ |
| F | F | Cl | H | H | NCH₃H |
| Cl | H | Cl | H | H | NCH₃H |
| F | F | Cl | Cl | H | NCH₃H |
| Cl | H | Cl | Cl | H | NCH₃H |
| Cl | F | Cl | CH₃ | H | OC₂H₅ |
| Cl | H | CH₃ | CH₃ | H | OC₂H₅ |
| F | F | CH₃ | CH₃ | H | N(CH₃)₂ |
| Cl | H | CH₃ | CH₃ | H | H(CH₃)₂ |
| F | F | CH₃ | Cl | CH₃ | OC₂H₅ |
| H | Cl | CH₂ | Cl | CH₃ | OC₂H₅ |
| F | Cl | CH₃ | Cl | CH₃ | OC₂H₅ |
| F | F | CH₃ | Cl | CH₃ | N(CH₃)₂ |
| Cl | H | CH₃ | Cl | CH₃ | N(CH₃)₂ |
| Cl | H | CH₃ | Cl | CH₃ | CH₃ |
| F | F | CH₃ | Cl | CH₃ | CH₃ |

TABLE C

| X | X¹ | Y | R | A |
|---|---|---|---|---|
| F | F | CH₃ | Cl | —CH=CH—CH=CH— |
| Cl | H | CH₃ | Cl | —CH=CH—CH=CH— |
| H | Cl | CH₃ | N(CH₃)₂ | —CH=CH—CH=CH— |
| F | F | CH₂ | N(CH₃)₂ | —CH=CH—CH=CH— |
| F | H | CH₃ | N(CH₃)₂ | —CH=CH—CH=CH— |
| F | F | CH₃ | OCH₃ | —CH=CH—CH=CH— |
| Cl | H | CH₃ | OCH₃ | —CH=CH—CH=CH— |
| H | F | CH₃ | OCH₃ | —CH=CH—CH=CH— |
| F | F | CH₃ | Cl | —(CH₂)₄— |
| F | H | CH₃ | Cl | —(CH₂)₄— |
| Cl | H | CH₃ | Cl | —(CH₂)₄— |
| F | F | CH₃ | N(CH₃)₂ | —(CH₂)₄— |
| H | Cl | CH₃ | N(CH₃)₂ | —(CH₂)₄— |
| F | F | Cl | Cl | —CH=CH—CH=CH— |

TABLE C-continued

| X | X¹ | Y | R | A |
|---|---|---|---|---|
| Cl | H | Cl | Cl | —CH=CH—CH=CH— |
| H | F | Cl | Cl | —CH=CH—CH=CH— |
| F | H | Cl | N(CH₃)₂ | —CH=CH—CH=CH— |
| H | Cl | Cl | N(CH₃)₂ | —CH=CH—CH=CH— |
| F | F | Cl | N(CH₃)₂ | —CH=CH—CH=CH— |
| H | Cl | Cl | OCH₃ | —CH=CH—CH=CH— |
| F | F | Cl | OCH₃ | —CH=CH—CH=CH— |
| F | F | Cl | Cl | —(CH₂)₄— |
| Cl | H | Cl | Cl | —(CH₂)₄— |
| H | F | Cl | Cl | —(CH₂)₄— |
| F | F | Cl | N(CH₃)₂ | —(CH₂)₄— |
| H | Cl | Cl | N(CH₃)₂ | —(CH₂)₄— |
| F | H | Cl | N(CH₃)₂ | —(CH₂)₄— |

The most preferred compounds within the scope of the present invention can be represented by the following formula

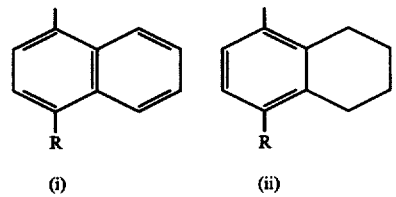

wherein X, X¹, Y, Y¹, Y² and B are as above.

The most pesticidally effective compounds are those in which X and X¹ are chloro or fluoro or in which X is chloro or fluoro while X¹ is hydrogen. It is necessary for these substituents to be at the ortho positions of the benzoyl moiety. It is preferred to have the Y and Y¹ substituent in the three and five positions of the phenyl ring. The most effective compounds are those when Y²=hydrogen, Y=Y¹=chloro or methyl or Y=-methyl and Y¹=chloro or hydrogen; when Y²=-methyl, Y=methyl and Y¹=chloro.

The most pesticidally effective B moieties are (i) and (ii).

(i)    (ii)

It is preferred to have a R substituent at carbon four of the 1-naphthyl or 5,6,7,8-tetrahydro-1-naphthyl moiety. The highest activity was observed when this substituent is chloro, methoxy or dimethylamino group.

The novel compositions of this invention can be conveniently prepared by two different methods. In the first method a bicyclooxyaniline is reacted with an arylisocyanate as illustrated below for the preparation of a 1-(bicyclooxyphenyl)-3-benzoyl urea:

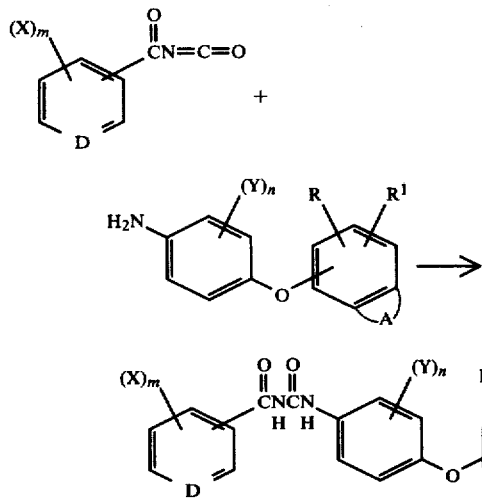

wherein: D, X, Y, n R, R¹, m and A are as previously described.

Alternatively, the compositions may be prepared through the reaction of a bicyclooxyphenylisocyanate with an amide according to the following reaction:

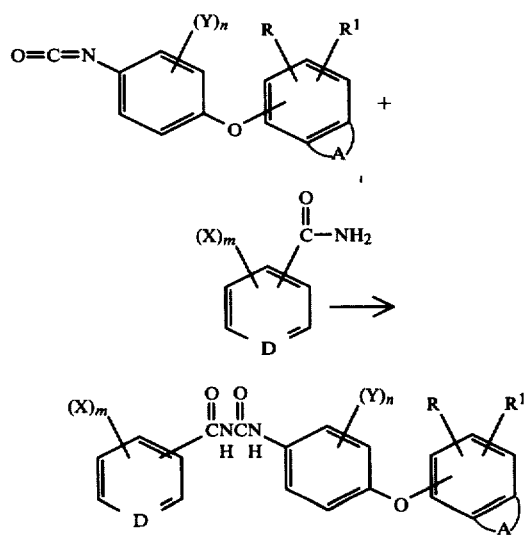

wherein: D, X, Y, n, R, R¹, m and A are as described previously.

In general, the reactions illustrated in both methods proceed smoothly without the need of additional reagents. However, the use of an organic solvent is preferred. Generally any solvent which is inert towards the reactants is suitable, although aromatic hydrocarbon and halogenated hydrocarbon solvents are preferred. Such solvents as toluene and 1,2-dichloroethane are especially preferred. These reactions will, in general, occur over a wide temperature range.

The intermediates shwn in the two methods for the preparation of the compositions of this invention can be prepared according to known procedures. For example, the substituted benzoylisocyanates are prepared from the substituted benzamides following the general procedure of Speziale et al., *J. Org. Chem.*, 27, 3742 (1962).

The benzamides themselves are either available commercially or can also be prepared according to known processes.

The anilines can be prepared according to the two step sequence illustrated below:

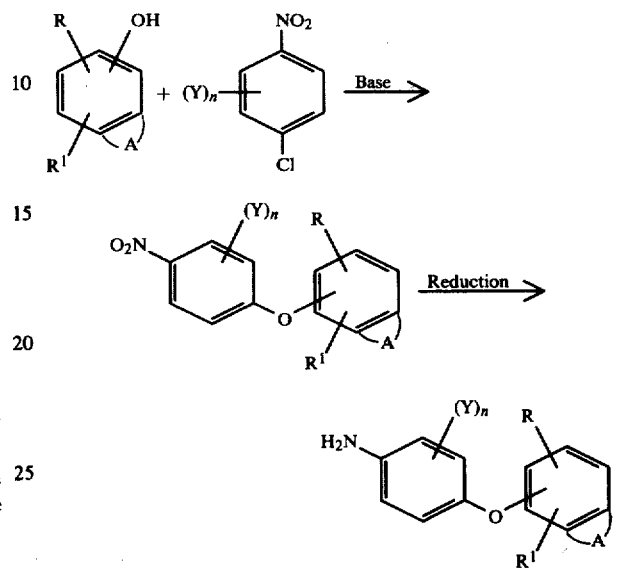

wherein: Y, R, R¹, n and A are as previously defined.

The reaction of the bicyclic phenol with a 4-chloro nitrobenzene proceeds in the presence of a base in an inert solvent at an elevated temperature to afford the nitro-ether.

Suitable bases include sodium hydride, potassium hydroxide and potassium carbonate. Suitable solvents include toluene, dimethylformamide and dimethylsulfoxide. If the reaction is heterogeneous a phase-transfer agent such as quaternary ammonium halide or crown ethers complex may be added.

The reduction of the nitro ether to the aniline can be accomplished under a hydrogen atmosphere using a heterogeneous hydrogenation catalyst. Such catalysts include platinum or palladium on an inert support or a Raney nickel catalyst. In general these reductions can be preformed under a wide range of temperatures and pressures. However, it is preferrable to use a pressure range 80–120 psi at ambient temperature. The solvents of choice include aromatic hydrocarbons, such as toluene or alcohols such as ethanol. Alternatively, this reduction may also be accomplished by a chemical reductant such as a transistion metal or its salts in a mineral acid solution. In general tin or iron and their salts in hydrochloric acid are preferred. A co-solvent such as dioxane or alcohols may be added to improve the reactant solubility in the reaction medium. The aniline can be converted to the isocyanate by the reaction with phosgene employing generally accepted procedures.

Both the bicyclic phenols and the nitrochlorobenzenes are available commercially or may be prepared by well known methods from the chemical literature.

As hereinbefore indicated and as set forth in the examples, the compositions of this invention are useful as insecticides and acaricides in certain cases are more effective than known benzoyl ureas.

The following examples are illustrative:

EXAMPLE 1

Preparation of 2,6-Difluorobenzoylisocyanate

A mixture containing 30.26 g (0.193 moles) of 2,6-difluorobenzamide in 250 ml of 1,2-dicloroethane was placed under an atmosphere of nitrogen and cooled to 5° C. (internal temp.). To this was then added dropwise a solution of 24.0 ml (34.8 g, 0.27 moles) of oxalyl chloride in 50 ml of 1,2-dichloroethane. During this addition the internal temperature was maintained below 10° C. The resulting reaction mixture was then stirred for ½ hour in an ice bath. The ice bath was removed and the reaction mixture allowed to warm to room temperature. After stirring at room temperature to 1½ hours the reaction mixture was slowly heated to reflux. After refluxing for 5 hours the reaction mixture was allowed to cool to room temperature. Removal of the solvent in vacuo afforded 31.77 g of an orange oil. NMR (CDCl$_3$): δ6.6–7.7 (m); IR (CHCl$_3$): 3370,2990,2220,1770,1747,1685,1605,1450 cm$^{-1}$.

EXAMPLE 2

Preparation of 1-(4-[4-Chloro-1-naphthoxyl]-3,5-dichlorophenyl)-3-(2,6-difluorobenzoyl) Urea

Part A: Preparation of 4-(4-chloro-1-naphthoxy)-3,5-dichloro-1-nitrobenzene To a mixture containing 28.02 g (0.203 mole) of anhydrous potassium carbonate and 30.26 g (0.134 mole) of 3,4,5-trichloro-1-nitrobenzene in 300 ml dry DMF under an atmosphere of nitrogen and at room temperature was added 30.04 g (0.168 mole) of 4-chloro-1-naphthol. The flask was then placed in an oil bath which was heated. An internal reaction temperature of 105° C. was reached and maintained for 20 hours. After cooling the reaction mixture to room temperature most of the DMF was removed under vacuum. The residue was taken up in 1.5 L of 1:1 EtOAc to Et$_2$O and 300 ml of H$_2$O. The layers were separated and washed twice with 5% NaOH, twice with H$_2$O, and finally once with a saturated aqueous NaCl solution. After drying over anhydrous Na$_2$SO$_4$ removal of the solvents afforded 48.73 g of a dark brown solid. This was recrystallized twice from hexane-ethyl acetate to afford 15.84 g of pale yellow needles; mp 121.5°–123° C. NMR (COCl$_3$): δ6.18 (d, J=8 Hz, 1H), 7.25 (d, J=8 Hz 1H) 8.4–8.7 (m, 2H), 8.0–8.5 (m, 4H, contains 8.25 [S]).

The following nitro ethers were obtained in a similar manner. Their melting points are also given. 3-chloro-4-(1-naphthoxy)-1-nitrobenzene, 79°–81° C.; 3-chloro-4-(4-chloro-1-naphthoxy)nitrobenzene, 156°–157° C.; 3-chloro-4-(6-bromo-2-naphthoxy)nitrobenzene, 128°–131° C.; 3-chloro-4-(1,6-dibromo-2-naphthoxy)nitrobenzene, 152°–154° C.; 3,5-dichloro-4-(1-naphthoxy)nitrobenzene, 100°–101° C.; 3-chloro-4-(5,6,7,8-tetrahydro-1-naphthoxy)-1-nitrobenzene, 156°–157° C.; 4-(1-naphtoxy)-3-trifluoromethyl-1-nitrobenzene, oil; 3,5-dichloro-4-(4-chloro-1-naphtoxy)-1-nitrobenzene, 121.5°–123° C.; 3,5-dichloro-4-(2-naphthoxy)-1-nitrobenzene, 118.5°–119° C.; 4-(4-chloro-1-naphthoxy)-3-trifluoromethyl-1-nitrobenzene, 77°–78.5° C.; 3-methyl-4-(1-naphthoxy)-1-nitrobenzene, oil; 4-(1-naphthoxy)-3-methyl-1-nitrobenzene, oil; 4-(4-chloro-1-naphthoxy)-3-methyl-1-nitrobenzene, 97°–98° C.; 3-chloro-4-(2,4-dichloro-1-naphthoxy)-1-nitrobenzene, 131°–132° C.; 3,5-dichloro-4-(6-bromo-2-naphthoxy)-1-nitrobenzene, 181°–183° C.; 3,5-dichloro-4-(2,4-dichloro-1-naphthoxy)-1-nitrobenzene, 128°–130°; 3,5-dichloro-4-(4-methoxy-1-naphthoxy)-1-nitrobenzene, 131°–132° C.; 3-chloro-4-(4-[N,N-dimethylamino]-1-naphthoxy)-1-nitrobenzene, 92°–94° C.; 3-chloro-4-(4-[dimethyl sulfamido]-1-naphthoxy)-1-nitrobenzene, 196°–197°; 4-(1-naphthoxy)-1-nitrobenzene, 140° C.; 2-(1,6-dibromo-2-naphthoxy)-5-nitrotoluene, 143°–146° C.; 3,5-dichloro-4-(5,6,7,8-tetrahydro-1-naphthoxy)-1-nitrobenzene, 138°–141° C.; 3,5-dichloro-4-(2,3-dihydro-2,2-dimethyl-7-benzofuranyloxy)-1-nitrobenzene, 105°–110° C.; 4-(4-chloro-1-naphthoxy)-1-nitrobenzene, 78°–82° C.; 4-(4-chloro-5,6,7,8-tetrahydro-1-naphthoxy)-3,5-dichloroaniline, 151°–154° C.; 4-(4-chloro-5,6,7,8-tetrahydro-1-naphthoxy)-3-methyl-1-nitrobenzene, 117°–120° C.; 3-chloro-4-(4-chloro-5,6,7,8-tetrahydro-1-naphthoxy)-1-nitrobenzene, 92°–96° C.; 3,5-dichloro-4-(4-dimethylamino-5,6,7,8-tetrahydro-1-naphthoxy)-1-nitrobenzene; 2-(4-dimethylamino-5,6,7,8-tetrahydro-1-naphthoxy)-5-nitrotoluene; 2-(4-methoxy-1-naphthoxy)-5-nitrotoluene, 154°–157° C.; 3-chloro-4-(4-methoxy-1-naphthoxy)-1-nitrobenzene, 124°–128° C.; N-(4-chlorophenyl)-4-(2-chloro-4-nitrophenoxy)-1-naphthylene sulfonamide, 216°–217° C.; 4-(4-chloro-1-naphthoxy)-3,5-dimethyl-1-nitrobenzene, 145°–146° C.; 3-chloro-4-(4-chloro-1-naphthoxy)-5-methyl-1-nitrobenzene, 131°–132° C.; 4-(4-chloro-1-naphthoxy)-3-methoxy-1-nitrobenzene, 94°–95° C.; 4-(4-chloro-5,6,7,8-tetrahydro-1-naphthoxy)-1-nitrobenzene, 92°–93° C.; 3-methoxy-4-(4-methoxy-1-naphthoxy)-1-nitrobenzene, 118°–121° C.; 3-chloro-4-(4-chloro-1-naphthoxy)-2,5-dimethyl-1-nitrobenzene, 135°–137° C.; 3-chloro-4-(4-chloro-5,6,7,8-tetrahydro-1-naphthoxy)-2,5-dimethyl-1-nitrobenzene, 157°–158° C.; 3-chloro-4-(4-chloro-5,6,7,8-tetrahydro-1-naphthoxy)-5-methyl-1-nitrobenzene, 157°–159° C.; 3-chloro-2,5-dimethyl-4-(4-dimethylamino-5,6,7,8-tetrahydro-1-naphthoxy)-1-nitrobenzene, 110°–111° C.; 4-(4-dimethylamino-5,6,7,8-tetrahydro-1-naphthoxy)-3-methoxy-1-nitrobenzene, 110°–113° C.; 3,5-dimethyl-4-(4-dimethylamino-5,6,7,8-tetrahydro-1-naphthoxy)-1-nitrobenzene, 121°–122° C.; 3-chloro-4-(4-methoxy-1-naphthoxy)-5-methyl-1-nitrobenzene, 4-(4-chloro-1-naphthoxy)-3,5-dibromo-1-nitrobenzene, 163°–164.5° C.; 4-(4-chloro-5,6,7,8-tetrahydro-1-naphthoxy)-3,5-dibromo-1-nitrobenzene, 178°–180° C.; 5-chloro-4-(4-chloro-1-naphthoxy)-2-methyl-1-nitrobenzene, 127°–128° C.; 4-(4-chloro-1-naphthoxy)-2,5-dimethyl-1-nitrobenzene, 85°–87° C.; 5-chloro-4-(4-chloro-5,6,7,8-tetrahydro-1-naphthoxy)-2-methyl-1-nitrobenzene, 139°–140° C.; 4-(4-chloro-5,6,7,8-tetrahydro-1-naphthoxy)-2,5-dimethyl-1-nitrobenzene, 124°–125° C.

Part B: Catalytic Reduction of 4-(4-Chloro-1-naphthoxy)-3,5-dichloro-1-nitrobenzene A 0.56 rocking hydrogenerator was charged with a solution of 15.84 g of 4-(4-chloro-1-naphthoxy)-3,5-dichloro-1-nitrobenzene in 250 ml of toluene. To this was added 0.5 g at 5% Pt on carbon and the bomb sealed. Hydrogen was introduced to a pressure of 100 psi. The pressure of hydrogen was maintained between 80 and 100 psi until the hydrogen up takes ceased. The material was removed from the bomb and filtered through celite. Removal of the solvents from the filtrates afforded 13.99 g of white solid, mp 145°–147° C. NMR (DMSO-d$_6$): δ5.72 (broad S, 2H), 6.38 (d, J=8 Hz, 1H), 6.82 (S, 2H), 7.3–8.7 (m, 5H).

The following anilines were prepared in a similar manner. Their melting points are also given. 3-chloro-4-(2-naphtoxy)aniline, 82°–83° C.; 3-chloro-4-(4-chloro-1-naphthoxy)aniline, 95°–96° C.; 3-chloro-4-(1-naphthoxy)-aniline, oil; 3,5-dichloro-4-(1-naphthoxy)aniline, 108°–109° C.; 3-chloro-4-(5,6,7,8-tetrahydro-1-naphthoxy)aniline, 62°–63° C.; 3-chloro-4-(2,3-dihydro-2,2-dimethyl-7-benzofuranyloxy)-aniline, 102°–104° C.; 3-chloro-4-(6-bromo-2-naphthoxy)-aniline, 112°–113° C.; 3-chloro-4-(1,6-dibromo-2-naphthoxy)-aniline, 121°–123° C.; 3,5-dichloro-4-(2-naphthoxy)aniline, 100°–102° C.; 3-trifluoromethyl-4-(1-naphthoxy)aniline, oil; 3-trifluoromethyl-4-(4-chloro-1-naphthoxy)aniline, 75° C.; 3-methyl-4-(1-naphthoxy)aniline, oil; 3-chloro-4-(2,4-dichloro-1-naphthoxy)aniline; 3,5-dichloro-4-(6-bromo-2-naphthoxy)aniline, 164°–166° C.; 3,5-dichloro-4-(4-methoxy-1-naphthoxy)aniline, 168°–169° C.; 3-chloro-4-(2,2-dimethyl-1,3-benzodioxolanyl-4-oxy)-1-aniline, 112°–114°, 4-(1,6-dibromo-2-naphthoxy)-3-methylaniline, 145°–150° C.; 3,5-dichloro-4-(2,3-dihydro-2,2-dimethyl-7-benzofuranyloxy)-1-aniline, 140°–145° C.; 4-(4-chloro-5,6,7,8-tetrahydro-1-naphtoxy)-3,5-dichloroaniline; 4-(4-chloro-5,6,7,8-tetrahydro-1-naphthoxy)-3-methylaniline, 82°–83° C.; 3,5-dichloro-4-(4-dimethylamino-5,6,7,8-tetrahydro-1-naphthoxy)aniline, 117°–120° C.; 3-chloro-4-(4-chloro-5,6,7,8-tetrahydro-1-naphthoxy)aniline, 70°–73° C.; 4-(4-chloro-1-naphthoxy)-3,5-dimethylaniline, 84°–88° C.; 3-chloro-4-(4-chloro-1-naphthoxy)-5-methylaniline, oil; 3-chloro-4-(4-methoxy-1-naphthoxy)aniline, 100°–102° C.; 4-(4-methoxy-1-naphthoxy)-3-methylaniline, 100°–102° C.; 4-(4-chloro-5,6,7,8-tetrahydro-1-naphthoxy)-3-methoxy aniline, 105°–107° C.; 3-methoxy-4-(4-methoxy-1-naphthoxy)aniline, 98°–101° C.; 3-chloro-4-(4-chloro-1-naphthoxy)-5-methylaniline, 111°–113° C.; 3-chloro-4-(4-chloro-1-naphthoxy)-2,5-dimethylaniline, 118°–125° C.; 3-chloro-4-(4-chloro-5,6,7,8-tetrahydro-1-naphthoxy)-5-methylaniline, 161°–162° C.; 3-chloro-2,5-dimethyl-4-(4-dimethylamino-5,6,7,8-tetrahydro-1-naphthoxy)aniline; 124°–126° C.; 4-(4-dimethylamino-5,6,7,8-tetrahydro-1-naphthoxy)-3-methoxyaniline, 120°–125° C.; 3,5-dimethyl-4-(4-dimethylamino-5,6,7,8-tetrahydro-1-naphthoxy)aniline, 102°–105° C.; 3-chloro-4-(4-methoxy-1-naphthoxy)-5-methylaniline, 126°–128° C.

Part C: Chemical Reduction of 4-(4-chloro-1-naphthoxy)-3,5-dichloro-1-nitrobenzene 37.47 g (0.1 moles) of 3,5-dichloro-4-(4-chloro-1-naphthoxy)nitrobenzene were added carefully to an 80° C. solution of 75.6 g (0.335 moles) of stannous chloride, 67 ml of HCl, and 50 ml of dioxane. (Mechanical stirrer needed because of resulting thick suspension). The suspension was stirred an additional 30 minutes at reflux. The reaction was cooled and then poured into a beaker containing 134 g (3.3 moles) of NaOH in 340 ml of H2O with an equal amount of ice. A white solid was filtered off, taken up in CH2Cl2 and dried. Removal of the solvents afforded 32.21 g of a white solid.

The following anilines were prepared in a similar manner. Their melting points are also given. 3-methyl-4-(4-chloro-1-naphthoxy)aniline; 75° C.; 3-chloro-4-(4-[N,N-dimethylamino]-1-naphthoxy)aniline, oil; N,N-dimethyl-4-(2-chloro-4-aminophenoxy)-1-naphthalene sulfonamide; 4-(1-naphthoxy)aniline, oil; 3,5-dichloro-4-(5,6,7,8-tetrahydro-1-naphthoxy)-aniline; 106°–112° C.; 4-(4-chloro-1-naphthoxy)aniline, oil; 3-chloro-4-(4-morpholino sulfonamido-1-naphthoxy)-aniline; 4-(4-chloro-1-naphtoxy)-3-methoxyaniline, oil; 3-chloro-4(4-chloro-5,6,7,8-tetrahydro-1-naphthoxy)-2,5-dimethylaniline, 111°–116° C.; 4-(4-chloro-1-naphthoxy)-3,5-dibromoaniline; 168°–171° C.; 4-(4-chloro-5,6,7,8-tetrahydro-1-naphthoxy)-3,5-dibromoaniline; 108°–111° C.; 5-chloro-4-(4-chloro-1-naphthoxy)-2-methylaniline; 4-(4-chloro-1-naphthoxy)-2,5-dimethylaniline, 96°–98° C.

Part D: Preparation of 1-(4-[4-Chloro-1-naphthoxy]-3,5-dichlorophenyl)-3-(2,6-difluorobenzoyl)urea A solution containing 2.25 g (6.6 m moles) of 4-(4-chloro-1-naphthoxy)-3,5-dichloroaniline in 45 ml of toluene was placed under a nitrogen atmosphere and heated to 70° C. via an addition funnel was then added 1.82 g (9.9 m moles) of 2,6-difluorobenzoylisocyanate in 5 ml of toluene. The resulting mixture was then stirred at 70° C. for 45 min. and then cooled to room temperature. It was then cooled below 0° C. and filtered. The collected white white solid was dried under vacuum to afford 1.86 g of the desired product, m.p. 237°–239° C. NMR: (DMSO-d$_6$): δ6.47 (d, J=8 Hz, 1H)- 7.0–8.6 (m, 10H), 10.40 (broad s, 1H), 11.60 (broad s, 1H).

EXAMPLES 3–210

In a manner similar to that of the previous example, other benzoyl ureas were also prepared. The following examples are further illustrative of the preparation of two specific compositions identified as examples 114 and 162 respectively.

EXAMPLE 114

Preparation of 3-(4-[4-Chloro-5,6,7,8-tetrahydro-1-naphthoxy]-3,5-dimethylphenyl)-1-(2-chlorobenzoyl) urea

Part A: Preparation of 4-(4-chloro-5,6,7,8-tetrahydro-1-naphthoxy)-3,5-dimethyl-1-nitrobenzene To a solution of 35.62 g (0.19 mole) of 4-chloro-3,5-dimethyl-1-nitrobenzene and 38.54 g (0.21 mole) of 4-chloro-5,6,7,8-tetrahydro-1-naphthol in 300 mL of dry DMF under an atmosphere of nitrogen and at room temperature was added 29.16 g (0.21 mole) of anhydrous potassium carbonate. The resulting reaction mixture was heated to 140° C. (internal). The reaction mixture was then heated between 140° and 150° C. for 40 hrs. The reaction mixture was then cooled to room temperature. The DMF was removed on a rotary evaporator in vacuo. The remaining dark brown semi-solid was dissolved in 500 mL of hot toluene and filtered. The collected solids were thoroughly washed with hot toluene. The toluene washings were combined with the toluene filtrate and the solvents removed to afford 34.8 g of dark brown solid. Recrystallization from hot hexane containing a little ethylene acetate along with the use of decolorizing carbon afforded 22.04 g of pale yellow solid; m.p. 176°–179° C. NMR (CDCl$_3$): δ1.7–2.0 (m, 4H), 2.20 (S, 6H), 2.7–3.0 (m, 4H), 5.95 (d, J=9 Hz, 1H), 6.95 (d, J=9 Hz, 1H), 8.02 (S, 2H).

Part B: Preparation of 4-(4-Chloro-5,6,7,8-tetrahydro-1-naphthoxy)-3,5-dimethylaniline A 1 L rocking Parr hydrogenator was charged with a solution containing 19.11 g of 4-(4-chloro-5,6,7,8-tetrahydro-1-naphthoxy)-3,5-dimethyl-1-nitrobenzene in 600 mL of toluene. To this was then added 1.0 g of 5% platinum on carbon. This was then placed under an atmosphere of hydrogen at 100 psi. The internal pressure was maintained between 80 and 100 psi while hydrogen uptake continued. When the hydrogen uptake ceased, the contents of the hydrogenator were removed and the vessel washed with toluene. The washings were combined with the reaction mixture. This was then filtered through celite. Removal of the solvents afforded 17.30 g of pale yellow solid. mp 126°–135° C. NMR(CDCl$_3$): δ1.6–1.8 (m, 4H), 2.0 (S, 6H), 2.6–2.9 (m, 4H), 3.45 (S, 2H), 6.13 (d, J=9 Hz, 1H), 6.37 (S, 2H), 6.93 (d, J=9 Hz, 1H).

Part C: Preparation of 3-(4-[4-Chloro-5,6,7,8-tetrahydro-1-naphthoxy]-3,5-dimethylphenyl)-1-(2-chlorobenzoyl) urea To a solution containing 3.0 g of 4-(4-chloro-5,6,7,8-tetrahydro-1-naphthoxy)-3,5-dimethylaniline in 40 mL of toluene under an atmosphere of nitrogen and heated to 70° C. (internal) was slowly added a solution containing 2.7 g of 2-chlorobenzoyl isocyanate in 5 mL of toluene. The resulting mixture was heated at 70° C. for ½ hour. The reaction mixture was cooled to 0° C. and filtered. The collected solid was washed with toluene and then hexane. It was dried under vacuum to afford 3.58 g of a white solid, mp. 224°–226° C. NMR (DMSO-d$_6$): 1.7–2.2 (m, 10H, contains singlet at 2.03), 2.7–3.0 (m, 4H), 6.07 (d, J=9 Hz, 1H), 7.07 (d, J=9 Hz, 1H), 7.07 (d, J=9 Hz, 1H), 7.4–7.7 (m, 4H), 10.38 (S, 1H), 11.20 (S, 1H).

EXAMPLE 162

Preparation of 3-(3-chloro-4-[2,3-dihydro-2,2-dimethyl-7-benzofuranyloxy]phenyl)-1-(2,6-difluorobenzoyl) urea

Part A: Preparation of 3-Chloro-4-(2,3-dihydro-2,2-dimethyl-7-benzofuranyloxy)-1-nitrobenzene To a mixture containing 32.63 g (0.236 mole) of anhydrous potassium carbonate and 30.41 g (0.158 mole) of 3,4-dichloro-1-nitrobenzene in 250 ml of dry DMF at room temperature and under an atmosphere of nitrogen was added 30.88 g (0.188 mole) of 2,3-dihydro-2,2-dimethyl-7-hydroxybenzofuran. The reaction mixture was then placed in an oil bath and heated to 110° C. for 20 hours The reaction mixture was cooled to room temperature. The DMF was removed under vacuum. The residue was dissolved in 1.5 L of 1:1 ethylacetate:ether and 300 ml of water. The layers were separated. The organic layer was washed twice with 5% NaOH, twice with H$_2$O and once with a saturated aqueous NaCl solution. After drying over anhydrous Na$_2$SO$_4$, removal of the solvents afforded 48.42 g of a light tan solid. This was recrystallized from hexane:ethyl acetate to afford 44.19 g of white crystals mp 132°–133° C. NMR (CDCl$_3$): δ1.42 (s, 6H), 3.05 (s, 2H), 6.5–7.2 (m, 4H), 7.95 (doft, J=9, 2 Hz, 1H), 8.28 (d, J=2 Hz, 1H).

Part B: Preparation of 3-Chloro-4-(2,3-dihydro-2,2-dimethyl-7-benzofuranyloxy)aniline To a solution containing 42.5 g of 3-chloro-4-(2,3-dihydro-2,2-dimethyl-7-benzofuranyloxy)-1-nitrobenzene in 600 ml of toluene was added 1.5 g of 5% Pt on carbon. This mixture was then placed in a 1 L rocking hydrogenator. An atmosphere of hydrogen at 100 psi was introduced into the bomb. The pressure was maintained between 100 psi and 80 psi until the hydrogen uptake ceased. The contents were removed from the bomb and filtered through celite. Removal of the solvents from the filtrates afforded 34.91 g of white solid, mp 102°–104° C. NMR (CDCl$_3$) δ1.45 (s, 6H), 3.0 (s, 2H), 3.55 (broad s, 2H), 6.2–6.9 (m, 6H).

Part C: Preparation of 1-(3-Chloro-4-[2,3-dihydro-2,2-dimethyl-7-benzofuranyloxy]phenyl)-3-(2,6-difluorobenzoyl) urea Solution containing 4.0 g (13.8 m moles) of 3-chloro-4-(2,3-dihydro-2,2-dimethyl-7-benzofuranyloxy)aniline in 45 ml of toluene was placed under an atmosphere of nitrogen and heated to 70° C. To this was added 3.79 g (20 m moles) of 2,6-difluorobenzoyl isocyanate in 5 ml of toluene via an addition funnel. The resulting mixture was heated for 45 min. and then cooled to room temperature. The mixture was further cooled below 0° C. in a freezer and then filtered. The collected solid was washed with cold toluene. This was dried under vacuum to afford 5.43 g of the desired product as a white solid, mp 171° C. NMR (DMSO-d$_6$): δ1.40 (s, 6H), 3.05 (s, 2H), 6.3–8.0 (m, 10H), 10.20 (broad s, 1H), 11.47 (broad s, 1H).

In a similar manner 4-(4-benzothienyloxy)-3-chloroaniline is prepared through the condensation of 4-hydroxybenzothiophene with 3,4-dichloro-1-nitrobenzene in the presence of anhydrous potassium carbonate in hot DMF. This product is reduced either chemically with stannous chloride in hydrochloric acid using dioxane as a co-solvent or through catalytic hydrogenation to produce the desired aniline. In a similar manner 4-(4-benzothienyloxy)-3,5-dichloroaniline is prepared from 1,2,3-trichloro-5-nitrobenzene.

Tables I through VI below set forth the physical properties of each of the benzoyl ureas prepared by the processes of this invention:

TABLE I

PHYSICAL PROPERTIES OF 1-(4-[1-NAPHTHOXY]PHENYL)-3-BENZOYLUREAS

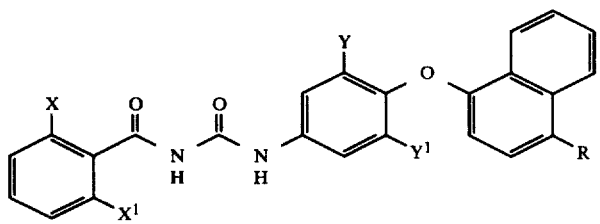

| | | | | | | | ELEMENTAL ANALYSIS | | | | | |
|---|---|---|---|---|---|---|---|---|---|---|---|---|
| | | | | | | Molecular | CALCULATED | | | FOUND | | |
| Example | X | $X^1$ | Y | $Y^1$ | R | MP (°C.) | Formula | % C | % H | % N | % C | % H | % N |
| 2 | F | F | Cl | Cl | Cl | 237–239 | $C_{24}H_{13}Cl_3F_2N_2O_3$ | 55.25 | 2.51 | 5.37 | 55.56 | 2.46 | 5.36 |
| 3 | $CH_3$ | H | Cl | H | H | 227–230 | $C_{25}H_{19}ClN_2O_3$ | 69.68 | 4.44 | 6.50 | 69.32 | 4.36 | 6.57 |
| 4 | $CH_3$ | $CH_3$ | Cl | H | H | 227.5–230 | $C_{26}H_{21}ClN_2O_3$ | 70.18 | 4.76 | 6.30 | 69.68 | 4.85 | 6.30 |
| 5 | $CH_3$ | $CH_3$ | Cl | H | Cl | 239–241 | $C_{26}H_{20}Cl_2N_2O_3$ | 65.14 | 4.12 | 5.84 | 64.62 | 4.10 | 5.81 |
| 6 | $CF_3$ | H | Cl | H | H | 209–211 | $C_{26}H_{16}ClF_3N_2O_3$ | 61.92 | 3.33 | 5.78 | 61.88 | 3.26 | 5.61 |
| 7 | $OCH_3$ | H | Cl | H | H | 125–127 | $C_{25}H_{16}ClN_2O_4$ | 67.19 | 4.28 | 6.27 | 67.11 | 4.19 | 6.13 |
| 8 | $OCH_3$ | $OCH_3$ | Cl | H | H | 214–215 | $C_{26}H_{21}ClN_2O_5$ | | 476.1174 | | | 476.1139[1] | |
| 9 | $OCH_3$ | $OCH_3$ | Cl | H | Cl | 227–230 | $C_{26}H_{20}Cl_2N_2O_5$ | | 510.0741 | | | 510.0749[1] | |
| 10 | $CH_3$ | $CH_3$ | Cl | H | Cl | 239–241 | $C_{26}H_{20}Cl_2N_2O_3$ | 65.14 | 4.21 | 5.84 | 64.62 | 4.10 | 5.81 |
| 11 | Cl | H | Cl | Cl | H | 231.5–232.5 | $C_{24}H_{15}Cl_3N_2O_3$ | 59.34 | 3.11 | 5.77 | 59.62 | 3.15 | 5.78 |
| 12 | F | F | Cl | Cl | H | 227–229 | $C_{24}H_{14}Cl_2F_2N_2O_3$ | 59.15 | 2.90 | 5.75 | 59.57 | 2.85 | 5.57 |
| 13 | Cl | F | Cl | Cl | H | 237–237.5 | $C_{24}H_{14}Cl_3FN_2O_3$ | 57.22 | 2.80 | 5.56 | 57.78 | 2.88 | 5.57 |
| 14 | Cl | Cl | Cl | Cl | H | 246–248 | $C_{24}H_{14}Cl_4N_2O_3$ | 55.41 | 2.71 | 5.39 | 55.37 | 2.59 | 5.38 |
| 15 | Cl | Cl | Cl | Cl | Cl | 246 dec | $C_{24}H_{13}Cl_4FN_2O_3$ | 51.94 | 2.36 | 5.05 | 52.27 | 2.31 | 5.03 |
| 16 | F | Cl | Cl | Cl | Cl | 252–253.5 | $C_{24}H_{13}Cl_4FN_2O_3$ | 53.56 | 2.43 | 5.21 | 53.60 | 2.41 | 5.17 |
| 17 | Cl | H | Cl | Cl | Cl | 2405–245 | $C_{24}H_{14}Cl_4N_2O_3$ | 55.41 | 2.71 | 5.39 | 55.53 | 2.71 | 5.54 |
| 18 | Cl | H | H | $CF_3$ | H | 211–212.5 | $C_{25}H_{16}ClF_3N_2O_3$ | 61.93 | 3.33 | 5.78 | 61.23 | 2.94 | 5.70 |
| 19 | Cl | H | $CF_3$ | H | Cl | 207–209.5 | $C_{25}H_{15}Cl_2F_3N_2O_3$ | 57.82 | 2.91 | 5.40 | 57.44 | 2.81 | 5.56 |
| 20 | F | F | $CF_3$ | H | H | 224–225 | $C_{25}H_{15}F_3N_2O_3$ | 61.73 | 3.11 | 5.76 | 61.23 | 2.94 | 5.70 |
| 21 | F | F | $CF_3$ | H | Cl | 215–217 | $C_{25}H_{14}ClF_4N_2O_3$ | 57.65 | 2.71 | 5.38 | 57.46 | 2.69 | 5.30 |
| 22 | Cl | F | $CF_3$ | H | H | 233–236 | $C_{25}H_{15}ClF_4N_2O_3$ | 59.71 | 3.01 | 5.57 | 59.82 | 2.86 | 5.54 |
| 23 | Cl | F | $CF_3$ | H | Cl | 232.5–235 | $C_{25}H_{14}Cl_2F_3N_2O_3$ | 55.88 | 2.63 | 5.22 | 56.03 | 2.97 | 5.30 |
| 24 | Cl | Cl | $CF_3$ | H | H | 231–232.5 | $C_{25}H_{15}Cl_2F_3N_2O_3$ | 57.82 | 2.91 | 5.40 | 57.90 | 2.74 | 5.41 |
| 25 | Cl | Cl | $CF_3$ | H | Cl | 238.5–240 | $C_{25}H_{14}Cl_3F_3N_2O_3$ | 54.22 | 2.55 | 5.06 | 54.29 | 2.49 | 5.15 |
| 26 | Cl | H | $CH_3$ | H | H | 217–219 | $C_{25}H_{19}ClN_2O_3$ | 69.68 | 4.44 | 6.50 | 69.82 | 4.50 | 6.55 |
| 27 | F | F | $CH_3$ | H | H | 229–230 | $C_{25}H_{18}F_2N_2O_3$ | 69.44 | 4.20 | 6.48 | 69.36 | 4.11 | 6.44 |
| 28 | Cl | F | $CH_3$ | H | H | 207.5–209 | $C_{25}H_{18}ClFN_2O_3$ | 66.89 | 4.04 | 6.24 | 67.01 | 3.95 | 6.29 |
| 29 | Cl | Cl | $CH_3$ | H | H | 224–227.5 | $C_{25}H_{18}Cl_2N_2O_3$ | 64.53 | 3.90 | 6.02 | 63.72 | 3.72 | 6.07 |
| 30 | $OCH_3$ | $OCH_3$ | Cl | Cl | Cl | 236–236.5 | $C_{26}H_{19}Cl_3N_2O_5$ | 57.21 | 3.51 | 5.13 | 57.42 | 3.57 | 5.13 |
| 31 | $OCH_3$ | H | Cl | H | Cl | 202–204 | $C_{25}H_{18}Cl_2N_2O_4$ | 62.38 | 3.77 | 5.82 | 62.63 | 3.09 | 5.76 |
| 32 | Cl | F | Cl | Cl | $OCH_3$ | 232 dec | $C_{25}H_{16}Cl_3FN_2O_4$ | 56.25 | 3.02 | 5.25 | 56.41 | 2.86 | 5.19 |
| 33 | F | F | Cl | Cl | $OCH_3$ | 229 dec | $C_{25}H_{16}Cl_2F_2N_2O_4$ | 58.04 | 3.12 | 5.42 | 57.93 | 3.04 | 5.13 |
| 34 | Cl | H | Cl | Cl | $OCH_3$ | 237 dec | $C_{25}H_{17}Cl_3N_2O_4$ | 58.21 | 3.32 | 5.43 | 58.31 | 3.35 | 5.55 |
| 35 | Cl | $NO_2$ | Cl | H | Cl | 230 dec | $C_{24}H_{14}Cl_3N_3O_5$ | 54.31 | 2.66 | 7.92 | 53.27 | 2.59 | 8.29 |
| 36 | Cl | $NO_2$ | Cl | Cl | Cl | 250 dec | $C_{24}H_{13}Cl_4N_3O_5$ | 51.00 | 2.32 | 7.43 | 50.67 | 2.24 | 7.73 |
| 37 | $OCH_3$ | $OCH_3$ | Cl | Cl | $OCH_3$ | 213 dec | $C_{27}H_{22}Cl_3N_2O_6$ | 56.21 | 3.85 | 4.86 | 56.91 | 4.01 | 5.38 |
| 38 | F | F | $CH_3$ | H | Cl | 233 dec | $C_{25}H_{17}ClF_2N_2O_3$ | 64.31 | 3.67 | 6.00 | 64.03 | 3.49 | 5.92 |
| 39 | Cl | H | $CH_3$ | H | Cl | 211 dec | $C_{25}H_{18}Cl_2N_2O_3$ | | 464.0694 | | | 464.0700[1] | |
| 40 | Cl | F | $CH_3$ | H | Cl | 247 dec | $C_{25}H_{17}Cl_2N_2O_3$ | 62.12 | 3.55 | 5.80 | 62.06 | 3.47 | 5.70 |
| 41 | Cl | F | Cl | H | $N(CH_3)_2$ | 175 dec | $C_{27}H_{20}Cl_2FN_3O_3$ | | 511.0866 | | | 511.0874[1] | |
| 42 | F | F | Cl | H | $N(CH_3)_2$ | 212–213.5 | $C_{26}H_{20}ClF_2N_3O_3$ | 62.97 | 4.07 | 8.47 | 63.15 | 4.03 | 8.48 |
| 43 | Cl | H | Cl | H | $N(CH_3)_2$ | 185 dec | $C_{26}H_{20}Cl_2N_3O_3$ | | 493.0960 | | | 493.0973[1] | |
| 44 | Cl | Cl | Cl | H | $SO_2N(CH_3)_2$ | 242 dec | $C_{26}H_{20}Cl_3N_3O_5S$ | 52.67 | 3.40 | 7.09 | 52.60 | 3.37 | 6.89 |
| 45 | Cl | F | Cl | H | $SO_2N(CH_3)_2$ | 240 dec | $C_{26}H_{20}Cl_2FN_3O_5S$ | 54.17 | 3.50 | 7.29 | 54.14 | 3.35 | 7.13 |
| 46 | F | F | Cl | H | $SO_2N(CH_3)_2$ | 245 dec | $C_{26}H_{20}ClF_2N_3O_5S$ | 55.76 | 3.60 | 7.50 | 55.83 | 3.56 | 7.28 |
| 47 | Cl | H | Cl | H | $SO_2N(CH_3)_2$ | 220 dec | $C_{26}H_{21}Cl_2N_3O_5S$ | 55.96 | 3.79 | 7.52 | 55.46 | 3.72 | 7.52 |
| 48 | $CH_3$ | $CH_3$ | Cl | Cl | Cl | 224 dec | $C_{26}H_{19}Cl_3N_2O_3$ | 60.77 | 3.73 | 5.45 | 62.35 | 3.98 | 5.67[2] |
| 49 | $CH_3$ | H | Cl | Cl | Cl | 232 dec | $C_{25}H_{17}Cl_3N_2O_3$ | 60.88 | 3.43 | 5.61 | 59.97 | 3.35 | 5.60 |
| 50 | $OCH_3$ | H | Cl | Cl | Cl | 214 dec | $C_{25}H_{17}Cl_3N_2O_4$ | 58.21 | 3.32 | 5.43 | 57.03 | 3.14 | 5.32 |
| 51 | $CF_3$ | H | Cl | Cl | Cl | 225 dec | $C_{25}H_{14}Cl_3F_3N_2O_3$ | 54.22 | 2.55 | 5.06 | 54.28 | 2.40 | 5.03 |
| 52 | F | H | Cl | Cl | Cl | 213 dec | $C_{25}H_{14}Cl_3FN_2O_3$ | 57.22 | 2.80 | 5.56 | 57.09 | 2.59 | 5.55 |
| 53 | Cl | F | Cl | H | $SO_2N\text{-morpholine}$ | 183 dec | $C_{28}H_{22}Cl_2FN_3O_6S$ | 54.37 | 3.59 | 6.79 | 55.34 | 3.69 | 6.95 |
| 54 | Cl | H | Cl | H | $SO_2N\text{-morpholine}$ | 202 dec | $C_{28}H_{23}Cl_2N_3O_6S$ | 56.00 | 3.86 | 7.00 | 54.31 | 3.57 | 6.78[2] |

TABLE I-continued
PHYSICAL PROPERTIES OF 1-(4-[1-NAPHTHOXY]PHENYL)-3-BENZOYLUREAS

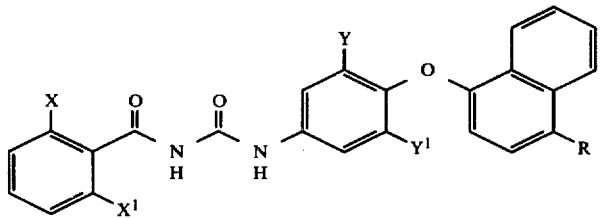

| Example | X | X$^1$ | Y | Y$^1$ | R | MP (°C.) | Molecular Formula | Calc %C | Calc %H | Calc %N | Found %C | Found %H | Found %N |
|---|---|---|---|---|---|---|---|---|---|---|---|---|---|
| 55 | F | F | Cl | H | SO$_2$N(morpholino) | 205 | C$_{28}$H$_{22}$ClF$_2$N$_3$O$_6$S | 55.86 | 3.86 | 6.98 | 55.70 | 3.56 | 6.97 |
| 56 | Cl | Cl | CH$_3$ | H | Cl | 260 dec | C$_{25}$H$_{17}$Cl$_3$N$_2$O$_3$ | 60.08 | 3.43 | 5.61 | 59.86 | 3.44 | 5.60 |
| 57 | OCH$_3$ | OCH$_3$ | CH$_3$ | H | Cl | 226 dec | C$_{27}$H$_{23}$ClN$_2$O$_5$ | 66.05 | 4.72 | 5.71 | 66.21 | 4.89 | 5.60 |
| 58 | OCH$_3$ | OCH$_3$ | H | H | Cl | 241 dec | C$_{26}$H$_{21}$ClN$_2$O$_5$ | 65.48 | 4.44 | 5.88 | 65.40 | 4.48 | 5.81 |
| 59 | H | F | CH$_3$ | H | Cl | 176–179 | C$_{24}$H$_{18}$ClFN$_2$O$_3$ | 66.89 | 4.04 | 6.24 | 66.74 | 4.01 | 6.20 |
| 60 | CH$_3$ | H | CH$_3$ | H | Cl | 197–198 | C$_{26}$H$_{21}$ClN$_2$O$_3$ | 70.18 | 4.76 | 6.30 | 70.25 | 4.74 | 6.23 |
| 61 | Cl | Cl | CH$_3$ | CH$_3$ | Cl | 253–255 | C$_{26}$H$_{19}$Cl$_3$N$_2$O$_3$ | 60.77 | 3.73 | 5.45 | 61.00 | 3.93 | 5.38 |
| 62 | Cl | F | CH$_3$ | CH$_3$ | Cl | 244–246 | C$_{26}$H$_{19}$Cl$_2$N$_2$O$_3$ | 62.79 | 3.85 | 5.63 | 62.97 | 3.88 | 5.67 |
| 63 | F | F | CH$_3$ | CH$_3$ | Cl | 226–229 | C$_{26}$H$_{19}$ClF$_2$N$_2$O$_3$ | 64.93 | 3.98 | 5.83 | 63.37 | 3.92 | 6.14[2] |
| 64 | Cl | NO$_2$ | CH$_3$ | H | Cl | 227 dec | C$_{25}$H$_{17}$Cl$_2$N$_3$O$_5$ | 58.84 | 3.36 | 8.23 | 57.17 | 3.42 | 8.62 |
| 65 | Cl | H | Cl | H | OCH$_3$ | 228 dec | C$_{25}$H$_{18}$Cl$_2$N$_2$O$_4$ | 62.38 | 3.77 | 5.82 | 62.20 | 3.92 | 5.84 |
| 66 | Cl | Cl |  | H | OCH$_3$ | 256 | C$_{26}$H$_{20}$Cl$_2$N$_2$O$_4$ | 63.04 | 4.07 | 5.66 | 63.20 | 4.14 | 5.49 |
| 67 | Cl | F | CH$_3$ | H | OCH$_3$ | 243 | C$_{26}$H$_{20}$ClFN$_2$O$_4$ | 65.20 | 4.21 | 5.85 | 65.45 | 4.33 | 5.74 |
| 68 | F | F | CH$_3$ | H | OCH$_3$ | 225 | C$_{26}$H$_{29}$F$_2$N$_2$O$_4$ | 67.52 | 4.36 | 6.06 | 67.69 | 4.28 | 6.03 |
| 69 | Cl | H | CH$_3$ | H | OCH$_3$ | 193 | C$_{26}$H$_{21}$ClN$_2$O$_4$ | 67.75 | 4.59 | 6.08 | 67.66 | 4.57 | 6.26 |
| 70 | F | F | H | CH$_3$ | OCH$_3$ | 115 dec | C$_{25}$H$_{17}$ClF$_2$N$_2$O$_4$ | 62.18 | 3.55 | 5.80 | 62.01 | 3.73 | 5.91 |
| 71 | Cl | F | H | Cl | OCH$_3$ | 239 dec | C$_{25}$H$_{17}$Cl$_2$FN$_2$O$_4$ | 60.13 | 3.43 | 5.61 | 59.99 | 3.43 | 5.64 |
| 72 | Cl | Cl | Cl | H | OCH$_3$ | 225 dec | C$_{25}$H$_{17}$Cl$_3$N$_2$O$_4$ | 58.21 | 3.32 | 5.43 | 57.95 | 3.35 | 5.43 |
| 73 | F | F | Cl | CH$_3$ | Cl | 229 dec | C$_{25}$H$_{16}$Cl$_2$F$_2$N$_2$O$_3$ | 58.89 | 3.22 | 5.59 | 60.33 | 3.35 | 5.51 |
| 74 | H | Cl | CH$_3$ | Cl | Cl | 245 dec | C$_{25}$H$_{17}$Cl$_3$N$_2$O$_3$ | 60.08 | 3.43 | 5.61 | 60.22 | 3.37 | 5.56 |
| 75 | Cl | F | OCH$_3$ | H | Cl | 195 dec | C$_{25}$H$_{17}$Cl$_2$FN$_2$O$_4$ | 60.13 | 3.43 | 5.61 | 60.40 | 3.34 | 5.53 |
| 76 | Cl | Cl | H | OCH$_3$ | Cl | 220 dec | C$_{25}$H$_{17}$Cl$_3$N$_2$O$_4$ | 58.21 | 3.32 | 5.43 | 57.60 | 3.13 | 5.43 |
| 77 | F | F | H | OCH$_3$ | Cl | 196 dec | C$_{25}$H$_{17}$ClF$_2$N$_2$O$_4$ | 62.18 | 3.55 | 5.80 | 61.92 | 3.46 | 5.77 |
| 78 | H | Cl | OCH$_3$ | H | Cl | 202 dec | C$_{25}$H$_{18}$Cl$_2$N$_2$O$_4$ | 62.38 | 3.77 | 5.82 | 62.02 | 3.70 | 5.71 |
| 79 | H | OC$_2$H$_5$ | CH$_3$ | H | Cl | 135–140° | C$_{27}$H$_{23}$ClN$_2$O$_4$ | 62.28 | 4.88 | 5.90 | 67.80 | 4.78 | 5.81 |
| 80 | Cl | Cl | Cl | CH$_3$ | Cl | 231 dec | C$_{25}$H$_{16}$Cl$_4$N$_2$O$_3$ | 56.20 | 3.02 | 5.24 | 54.79 | 2.80 | 5.24 |
| 81 | F | Cl | CH$_3$ | Cl | Cl | 237 dec | C$_{25}$H$_{16}$Cl$_3$FN$_2$O$_3$ | 57.99 | 3.12 | 5.41 | 58.00 | 3.02 | 5.39 |
| 82 | Cl | H | CH$_3$ | CH$_3$ | Cl | 226–229 | C$_{26}$H$_{20}$Cl$_2$N$_2$O$_3$ | 65.14 | 4.30 | 5.85 | 64.97 | 4.30 | 5.89 |
| 83 | F | F | H | OCH$_3$ | OCH$_3$ | 177 dec | C$_{26}$H$_{20}$F$_2$N$_2$O$_5$ | 65.27 | 4.21 | 5.86 | 65.06 | 4.19 | 6.04 |
| 84 | H | Cl | OCH$_3$ | H | OCH$_3$ | 115 dec | C$_{26}$H$_{21}$ClN$_2$O$_5$ | 65.48 | 4.44 | 5.88 | 64.59 | 4.33 | 6.07 |
| 85 | F | H | CH$_3$ | CH$_3$ | Cl | 234 dec | C$_{26}$H$_{20}$ClFN$_2$O$_3$ | 67.46 | 4.36 | 6.05 | 67.87 | 4.34 | 6.05 |
| 86 | F | H | Cl | CH$_3$ | Cl | 225 dec | C$_{25}$H$_{17}$Cl$_2$FN$_2$O$_3$ | 63.12 | 3.55 | 5.80 | 62.32 | 3.52 | 6.00 |
| 87 | Cl | H | CH$_3$ | CH$_3$ | OCH$_3$ | 245 dec | C$_{26}$H$_{20}$Cl$_2$N$_2$O$_4$ | 63.04 | 4.07 | 5.66 | 63.10 | 4.03 | 5.63 |
| 88 | Cl | Cl | CH$_3$ | Cl | OCH$_3$ | 234 dec | C$_{26}$H$_{19}$Cl$_3$N$_2$O$_4$ | 58.94 | 3.61 | 5.29 | 57.68 | 3.43 | 5.37 |
| 89 | Cl | F | Cl | CH$_3$ | OCH$_3$ | 219 dec | C$_{26}$H$_{19}$Cl$_2$FN$_2$O$_4$ | 60.83 | 3.73 | 5.46 | 60.90 | 3.73 | 5.46 |
| 90 | F | F | CH$_3$ | Cl | OCH$_3$ | 231 dec | C$_{26}$H$_{19}$ClF$_2$N$_2$O$_4$ | 62.84 | 3.85 | 5.64 | 62.72 | 3.77 | 5.65 |

[1] Exact mass measurement by high resolution mass spectroscopy
[2] Structure confirmed by spectroscopic data

TABLE II
PHYSICAL PROPERTIES OF 1-(4-[5, 6, 7, 8-TETRAHYDRO-1-NAPHTHOXY]PHENYL)-3-BENZOYLUREAS

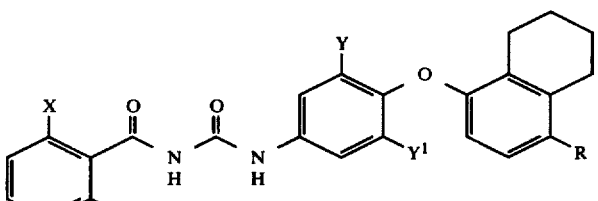

| Example | X | X$^1$ | Y | Y$^1$ | R | MP(°C.) | Molecular Formula | Calc %C | Calc %H | Calc %N | Found %C | Found %H | Found %N |
|---|---|---|---|---|---|---|---|---|---|---|---|---|---|
| 91 | Cl | Cl | Cl | H | H | 241–243 | C$_{24}$H$_{19}$Cl$_3$N$_2$O$_3$ | 58.85 | 3.91 | 5.72 | 59.13 | 3.87 | 5.71 |

TABLE II-continued

PHYSICAL PROPERTIES OF 1-(4-[5, 6, 7, 8-TETRAHYDRO-1-NAPHTHOXY]PHENYL)-3-BENZOYLUREAS

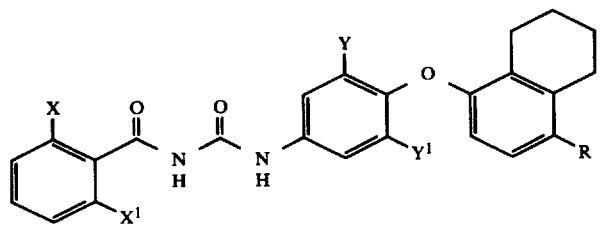

| Example | X | X¹ | Y | Y¹ | R | MP(°C.) | Molecular Formula | CALCULATED % C | % H | % N | FOUND % C | % H | % N |
|---|---|---|---|---|---|---|---|---|---|---|---|---|---|
| 92 | Cl | F | Cl | H | H | 216.5-217 | $C_{24}H_{19}Cl_2FN_2O_3$ | 60.90 | 4.05 | 5.92 | 61.49 | 3.93 | 5.83 |
| 93 | F | F | Cl | H | H | 208.5-209.5 | $C_{24}H_{19}ClF_2N_2O_3$ | 63.09 | 4.19 | 6.13 | 63.03 | 4.04 | 6.10 |
| 94 | Cl | H | Cl | H | H | 208.5-211.5 | $C_{24}H_{20}Cl_2N_2O_3$ | 63.30 | 4.43 | 6.15 | 63.27 | 4.30 | 6.24 |
| 95 | Cl | Cl | Cl | Cl | H | 263 dec | $C_{24}H_{18}Cl_4N_2O_3$ | 54.99 | 3.46 | 5.34 | 55.12 | 3.42 | 5.29 |
| 96 | Cl | F | Cl | Cl | H | 248 dec | $C_{24}H_{18}Cl_3FN_2O_3$ | 56.66 | 3.57 | 5.51 | 56.73 | 3.48 | 5.48 |
| 97 | F | F | Cl | Cl | H | 242 dec | $C_{24}H_{18}Cl_2F_2N_2O_3$ | 58.55 | 3.68 | 5.69 | 58.20 | 3.58 | 5.64 |
| 98 | Cl | H | Cl | Cl | H | 215 dec | $C_{24}H_{19}Cl_3N_2O_3$ | 58.85 | 3.91 | 5.72 | 58.80 | 3.96 | 5.66 |
| 99 | OCH₃ | OCH₃ | Cl | Cl | H | 211 dec | $C_{26}H_{24}Cl_2N_2O_5$ | 60.95 | 4.69 | 5.44 | 60.34 | 4.67 | 5.43 |
| 100 | Cl | H | Cl | Cl | H | 252 dec | $C_{24}H_{18}Cl_4N_2O_3$ | 54.99 | 3.46 | 5.34 | 55.05 | 3.35 | 5.25 |
| 101 | F | F | Cl | Cl | Cl | 260 dec | $C_{24}H_{17}Cl_3F_2N_2O_3$ | 54.83 | 3.26 | 5.33 | 54.85 | 3.18 | 5.26 |
| 102 | F | F | CH₃ | H | Cl | 230-234 | $C_{25}H_{21}ClF_2N_2O_3$ | 63.77 | 4.50 | 5.95 | 64.07 | 4.47 | 5.92 |
| 103 | Cl | H | CH₃ | H | Cl | 226-229 | $C_{25}H_{22}Cl_2N_2O_3$ | 63.98 | 4.72 | 5.97 | 63.82 | 4.71 | 5.88 |
| 104 | Cl | F | Cl | Cl | Cl | 265-266 | $C_{25}H_{17}Cl_4FN_2O_3$ | 53.16 | 3.16 | 5.17 | 53.08 | 3.08 | 5.18 |
| 105 | F | Cl | H | CH₃ | Cl | 250-252 | $C_{25}H_{21}Cl_2FN_2O_3$ | 61.61 | 4.34 | 5.75 | 61.63 | 4.25 | 5.62 |
| 106 | Cl | Cl | H | CH₃ | Cl | 267 dec | $C_{25}H_{21}Cl_3N_2O_3$ | 59.60 | 4.20 | 5.56 | 59.51 | 4.11 | 5.53 |
| 107 | Cl | Cl | Cl | Cl | Cl | 276 dec | $C_{24}H_{17}Cl_5N_2O_3$ | 51.60 | 3.07 | 5.01 | 51.26 | 2.95 | 5.05 |
| 108 | F | F | Cl | Cl | N(CH₃)₂ | 203-205 | $C_{26}H_{23}Cl_2F_2N_3O_3$ | 58.44 | 4.34 | 7.68 | 58.11 | 4.18 | 7.77 |
| 109 | Cl | F | Cl | Cl | N(CH₃)₂ | 221 dec | $C_{26}H_{23}Cl_3FN_3O_3$ | 56.69 | 4.21 | 7.63 | 56.43 | 4.27 | 7.80 |
| 110 | H | Cl | Cl | Cl | N(CH₃)₂ | 218 dec | $C_{27}H_{24}Cl_3N_3O_3$ | 58.61 | 4.54 | 7.89 | 58.68 | 4.64 | 7.90 |
| 111 | F | Cl | H | CH₃ | N(CH₃)₂ | 220-222 | $C_{27}H_{27}ClFN_3O_3$ | 65.39 | 5.49 | 8.47 | 65.32 | 5.37 | 8.45 |
| 112 | Cl | F | H | Cl | Cl | 250 dec | $C_{24}H_{18}Cl_3FN_2O_3$ | 56.77 | 3.57 | 5.52 | 57.11 | 3.52 | 5.46 |
| 113 | H | Cl | Cl | H | Cl | 231-233 | $C_{24}H_{19}Cl_3N_2O_3$ | 58.86 | 3.91 | 5.72 | 58.61 | 3.74 | 5.82 |
| 114 | H | Cl | CH₃ | CH₃ | Cl | 224-226 | $C_{26}H_{24}Cl_2N_2O_3$ | 64.60 | 5.00 | 5.80 | 64.45 | 5.02 | 5.91 |
| 115 | Cl | Cl | CH₃ | CH₃ | Cl | 238-241 | $C_{26}H_{23}Cl_3N_3O_3$ | 60.30 | 4.48 | 5.41 | 60.10 | 4.37 | 5.48 |
| 116 | Cl | F | CH₃ | CH₃ | Cl | 232-236 | $C_{26}H_{23}Cl_2FN_2O_3$ | 62.28 | 4.62 | 5.59 | 61.54 | 4.66 | 5.69 |
| 117 | F | F | CH₃ | CH₃ | Cl | 230-233 | $C_{26}H_{23}ClF_2N_2O_3$ | 64.39 | 4.78 | 5.78 | 63.20 | 4.62 | 6.04 |
| 118 | Cl | Cl | H | OCH₃ | Cl | 219-222 | $C_{25}H_{21}Cl_3N_2O_4$ | 57.76 | 4.07 | 5.39 | 56.09 | 3.75 | 5.582 |
| 119 | F | Cl | OCH₃ | H | Cl | 209-211 | $C_{25}H_{21}Cl_2FN_2O_4$ | 59.65 | 4.21 | 5.57 | 59.63 | 4.12 | 5.65 |
| 120 | F | F | H | OCH₃ | Cl | 210-212 | $C_{25}H_{21}ClF_2N_2O_4$ | 61.64 | 4.35 | 5.75 | 61.44 | 4.26 | 5.82 |
| 121 | Cl | H | H | OCH₃ | Cl | 181-184 | $C_{25}H_{22}Cl_2N_2O_4$ | 61.87 | 4.57 | 5.77 | 62.56 | 4.61 | 5.68 |
| 122 | F | F | CH₃ | H | N(CH₃)₂ | 178-182 | $C_{27}H_{27}F_2N_3O_3$ | 67.63 | 5.68 | 8.76 | 63.16 | 4.76 | 8.61 |
| 123 | Cl | Cl | Cl | Cl | N(CH₃)₂ | 237 dec | $C_{26}H_{23}Cl_4N_3O_3$ | 57.06 | 4.24 | 7.68 | 54.26 | 4.02 | 7.38 |
| 124 | Cl | H | H | CH₃ | N(CH₃)₂ | 178-180 | $C_{27}H_{28}ClN_3O_3$ | 67.85 | 5.91 | 8.79 | 66.22 | 5.54 | 8.71 |
| 125 | Cl | Cl | H | CH₃ | N(CH₃)₂ | 185 dec | $C_{27}H_{27}Cl_2N_3O_3$ | 63.29 | 5.31 | 8.20 | 59.43 | 4.63 | 7.77 |
| 126 | F | F | H | Cl | Cl | 220-223 | $C_{24}H_{18}Cl_2F_2N_2O_3$ | 63.59 | 4.00 | 6.18 | 58.68 | 3.61 | 5.79 |
| 127 | Cl | Cl | Cl | CH₃ | Cl | 248 dec | $C_{25}H_{20}Cl_4N_2O_3$ | 55.78 | 3.75 | 5.21 | 55.03 | 3.56 | 5.41 |
| 128 | Cl | F | CH₃ | Cl | Cl | 253 dec | $C_{25}H_{20}Cl_3FN_2O_3$ | 57.54 | 3.86 | 5.37 | 58.10 | 3.86 | 5.37 |
| 129 | F | F | Cl | CH₃ | Cl | 250 dec | $C_{25}H_{20}Cl_2F_2N_2O_3$ | 59.41 | 3.99 | 5.54 | 59.85 | 3.95 | 5.55 |
| 130 | Cl | H | CH₃ | Cl | Cl | 232 dec | $C_{25}H_{21}Cl_3N_2O_3$ | 59.60 | 4.20 | 3.56 | 59.96 | 4.19 | 5.56 |
| 131 | Cl | Cl | H | OCH₃ | N(CH₃)₂ | 193 dec | $C_{27}H_{27}Cl_2N_3O_4$ | 61.37 | 5.15 | 7.95 | 58.15 | 4.68 | 7.74 |
| 132 | F | Cl | OCH₃ | H | N(CH₃)₂ | 180 dec | $C_{27}H_{27}ClFN_3O_4$ | 63.34 | 5.32 | 8.21 | 63.16 | 5.29 | 8.06 |
| 133 | F | F | CH₃ | CH₃ | N(CH₃)₂ | 203 dec | $C_{28}H_{29}F_2N_3O_3$ | 68.14 | 5.92 | 8.51 | 66.62 | 5.92 | 8.51 |
| 134 | Cl | H | CH₃ | CH₃ | N(CH₃)₂ | 228 dec | $C_{28}H_{30}ClN_3O_3$ | 68.35 | 6.15 | 8.54 | 68.14 | 6.10 | 8.44 |
| 135 | Cl | Cl | CH₃ | CH₃ | N(CH₃)₂ | 212 dec | $C_{28}H_{29}Cl_2N_3O_3$ | 63.88 | 5.55 | 7.98 | 61.02 | 5.05 | 7.77 |
| 136 | F | F | OCH₃ | H | N(CH₃)₂ | 191-193 | $C_{27}H_{27}F_2N_3O_4$ | 65.44 | 5.49 | 8.48 | 65.40 | 5.31 | 8.38 |
| 137 | H | Cl | H | OCH₃ | N(CH₃)₂ | 165 | $C_{27}H_{28}ClN_3O_4$ | 65.65 | 5.71 | 8.51 | 65.70 | 5.66 | 8.44 |
| 138 | F | Cl | CH₃ | CH₃ | N(CH₃)₂ | 212 dec | $C_{28}H_{29}ClFN_3O_3$ | 65.94 | 5.73 | 8.24 | 65.17 | 5.69 | 7.95 |
| 139 | F | H | Cl | CH₃ | Cl | 218 dec | $C_{25}H_{21}Cl_2FN_2O_3$ | 61.61 | 4.34 | 5.75 | 61.78 | 4.32 | 5.82 |

TABLE III

PHYSICAL PROPERTIES OF 1-(4-[2-NAPHTHOXY]PHENYL)-3-BENZOYLUREAS

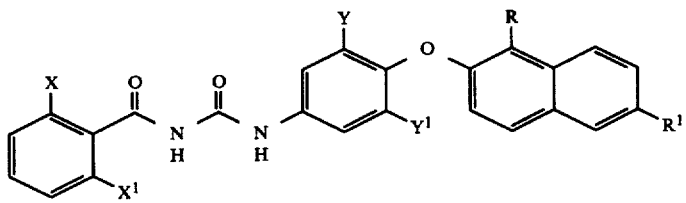

| Example | X | $X^1$ | Y | $Y^1$ | R | $R^1$ | MP(°C.) | Molecular Formula | Calculated %C | %H | %N | Found %C | %H | %N |
|---|---|---|---|---|---|---|---|---|---|---|---|---|---|---|
| 140 | Cl | H | Cl | Cl | H | H | 212–213.5 | $C_{24}H_{15}Cl_3N_2O_3$ | 59.34 | 3.11 | 5.77 | 59.33 | 2.99 | 5.89 |
| 141 | F | F | Cl | Cl | H | H | 187–189 | $C_{24}H_{14}Cl_2F_2N_2O_3$ | 59.15 | 2.90 | 5.75 | 58.76 | 2.85 | 5.80 |
| 142 | Cl | Cl | Cl | Cl | H | H | 218.5–222 | $C_{24}H_{14}Cl_4N_2O_3$ | 55.41 | 2.71 | 5.39 | 55.23 | 2.68 | 5.41 |
| 143 | $OCH_3$ | $OCH_3$ | Cl | H | Br | Br | 223–226.5 | $C_{26}H_{19}Br_2ClN_2O_5$ | 49.20 | 3.02 | 4.41 | 50.24 | 3.10 | 4.72[1] |
| 144 | $OCH_3$ | $OCH_3$ | Cl | H | H | Br | 205–209 | $C_{26}H_{20}BrClN_2O_5$ | 56.18 | 3.63 | 5.04 | 56.14 | 3.71 | 5.09 |
| 145 | Cl | F | Cl | Cl | H | H | 207.5–210 | $C_{24}H_{14}Cl_3FN_2O_3$ | 57.22 | 2.80 | 5.56 | 56.60 | 2.77 | 5.48 |
| 146 | Cl | Cl | Cl | Cl | H | Br | 250 dec | $C_{24}H_{13}BrCl_4N_2O_3$ | 48.11 | 2.19 | 4.68 | 47.80 | 2.17 | 4.80 |
| 147 | F | Cl | Cl | Cl | H | Br | 231 dec | $C_{24}H_{13}BrCl_3FN_2O_3$ | 49.47 | 2.25 | 4.81 | 49.80 | 2.23 | 4.83 |
| 148 | F | F | Cl | Cl | H | Br | 233 dec | $C_{24}H_{13}BrCl_2F_2N_2O_3$ | 50.91 | 2.31 | 4.95 | 50.93 | 2.26 | 4.96 |
| 149 | Cl | H | Cl | Cl | H | Br | 227 dec | $C_{24}H_{14}BrCl_3N_2O_3$ | 51.05 | 2.50 | 4.96 | 51.20 | 2.44 | 4.99 |
| 150 | Cl | $NO_2$ | Cl | H | Br | Br | 300 dec | $C_{24}H_{13}Br_2Cl_2N_3O_5$ | 84.07 | 2.00 | 6.44 | 44.22 | 1.98 | 6.99 |
| 151 | Cl | Cl | H | $CH_3$ | Br | Br | 222 dec | $C_{25}H_{16}Br_2Cl_2N_2O_3$ | 48.19 | 2.59 | 4.50 | 47.80 | 2.42 | 4.75 |
| 152 | F | F | $CH_3$ | H | Br | Br | 229–231 | $C_{25}H_{16}Br_2F_2N_2O_3$ | 50.86 | 2.73 | 4.75 | 50.77 | 2.65 | 4.80 |
| 153 | Cl | H | $CH_3$ | H | Br | Br | 217–219 | $C_{25}H_{17}Br_2ClN_2O_3$ | 51.05 | 2.91 | 4.76 | 51.05 | 2.70 | 4.87 |
| 154 | Cl | F | $CH_3$ | H | Br | Br | 232–234 | $C_{25}H_{16}Br_2ClFN_2O_3$ | 49.50 | 2.66 | 4.62 | 49.32 | 2.49 | 4.72 |
| 155 | $OC_2H_5$ | H | Cl | Cl | H | Br | 203–205 | $C_{26}H_{19}BrCl_2N_2O_4$ | 54.00 | 3.31 | 4.84 | 54.07 | 3.19 | 4.82 |
| 156 | $CH_3$ | H | Cl | H | H | H | 232–234 | $C_{25}H_{19}ClN_2O_3$ | 69.68 | 4.44 | 6.50 | 69.21 | 4.39 | 6.59 |
| 157 | $CH_3$ | $CH_3$ | Cl | H | H | H | 211.5–214 | $C_{25}H_{21}ClN_2O_3$ | 70.18 | 4.76 | 6.30 | 69.71 | 4.68 | 6.29 |
| 158 | H | $OCH_3$ | Cl | H | H | H | 153–154 | $C_{25}H_{19}ClN_2O_4$ | 67.19 | 4.28 | 6.27 | 67.11 | 4.29 | 6.13 |
| 159 | $OCH_3$ | $OCH_3$ | Cl | Cl | H | Br | 235 dec | $C_{26}H_{19}BrCl_2N_2O_4$ | 52.90 | 3.24 | 4.75 | 53.20 | 3.23 | 4.68 |
| 160 | $OCH_3$ | $OCH_3$ | Cl | H | H | H | 187–190 | $C_{26}H_{21}ClN_2O_4$ | 44.07 | 4.44 | 5.88 | 65.04 | 4.62 | 5.51 |

[1]Structure confirmed by spectroscopic data.

TABLE IV

PHYSICAL PROPERTIES OF 1-(4-[BICYCLOOXY]PHENYL)-3-BENZOYLUREAS

| Example | Structure | | | | MP(°C.) | Molecular Formula | Calculated %C | %H | %N | Found %C | %H | %N |
|---|---|---|---|---|---|---|---|---|---|---|---|---|

Structure:

![structure with dihydrobenzofuran]

| | X | $X^1$ | Y | $Y^1$ | | | | | | | | |
|---|---|---|---|---|---|---|---|---|---|---|---|---|
| 161 | Cl | H | H | Cl | 179.5–181 | $C_{24}H_{20}Cl_2N_2O_4$ | 61.15 | 4.28 | 5.94 | 60.85 | 4.18 | 5.97 |
| 162 | F | F | H | Cl | 171 | $C_{24}H_{19}ClF_2N_2O_4$ | 60.96 | 4.05 | 5.93 | 60.97 | 3.93 | 5.94 |
| 163 | F | Cl | Cl | H | 131–132 | $C_{24}H_{19}Cl_2FN_2O_4$ | 58.91 | 3.91 | 5.78 | 58.89 | 3.85 | 5.79 |
| 164 | Cl | Cl | Cl | H | 206–207 | $C_{24}H_{19}Cl_3N_2O_4$ | 56.99 | 3.79 | 5.54 | 57.32 | 3.93 | 5.10 |
| 165 | $OCH_3$ | $OCH_3$ | Cl | H | 213–214 | $C_{26}H_{26}ClN_2O_6$ | 62.84 | 5.03 | 5.64 | 62.63 | 5.09 | 5.76 |
| 166 | F | F | Cl | Cl | 208–214 | $C_{24}H_{18}Cl_2F_2N_2O_4$ | 56.82 | 3.58 | 5.52 | 59.21 | 3.85 | 5.09[1] |
| 167 | Cl | H | Cl | Cl | 190–196 | $C_{24}H_{19}ClN_2O_4$ | 56.99 | 3.79 | 5.54 | 56.65 | 3.64 | 5.73 |
| 168 | Cl | Cl | Cl | Cl | 214–220 | $C_{24}H_{18}Cl_3N_2O_4$ | 53.36 | 3.36 | 5.19 | 52.87 | 3.18 | 5.34 |
| 169 | F | Cl | Cl | Cl | 213–223 | $C_{24}H_{13}Cl_3FN_2O_4$ | 55.04 | 3.46 | 5.35 | 55.20 | 3.65 | 5.20 |

[1]Structure confirmed by spectral data.

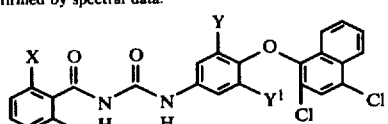

| | X | $X^1$ | Y | $Y^1$ | | | | | | | | |
|---|---|---|---|---|---|---|---|---|---|---|---|---|
| 170 | $OCH_3$ | $OCH_3$ | Cl | H | 309 dec | $C_{26}H_{19}Cl_3N_2O_5$ | 57.21 | 3.51 | 5.13 | — | — | — |
| 171 | F | F | Cl | Cl | 228–231 | $C_{24}H_{12}Cl_4F_2N_2O_3$ | 51.82 | 2.18 | 5.04 | 51.85 | 2.07 | 5.02 |
| 172 | Cl | F | Cl | Cl | 245 dec | CHClFNO | 50.34 | 2.11 | 4.89 | 50.48 | 2.05 | 4.85 |
| 173 | $OCH_3$ | $OCH_3$ | Cl | Cl | 227 dec | $C_{26}H_{18}Cl_4N_2O_5$ | 577.9920 | | | 577.9949[1] | | |

[1]Exact mass measurement by high resolution mass spectroscopy.

TABLE IV-continued
PHYSICAL PROPERTIES OF 1-(4-[BICYCLOOXY]PHENYL)-3-BENZOYLUREAS

| Example | Structure | MP(°C.) | Molecular Formula | ELEMENTAL ANALYSIS CALCULATED | | | FOUND | | |
|---|---|---|---|---|---|---|---|---|---|
| | | | | % C | % H | % N | % C | % H | % N |

Structure (Examples 174-176):

| Example | X | X¹ | MP(°C.) | Molecular Formula | % C calc | % H calc | % N calc | % C found | % H found | % N found |
|---|---|---|---|---|---|---|---|---|---|---|
| 174 | Cl | Cl | 195-196 | $C_{23}H_{18}Cl_3N_2O_5$ | 54.29 | 3.57 | 5.51 | 54.07 | 3.27 | 5.56 |
| 175 | F | F | 161-162 | $C_{23}H_{18}Cl_3N_2O_5$ | 54.29 | 3.57 | 5.51 | 54.07 | 3.27 | 5.57 |
| 176 | Cl | H | 187-188 | $C_{23}H_{18}Cl_2N_2O_5$ | 58.36 | 3.83 | 5.92 | 58.21 | 3.73 | 6.04 |

Structure (Examples 177-182):

| Example | X | X¹ | X² | MP(°C.) | Molecular Formula | % C calc | % H calc | % N calc | % C found | % H found | % N found |
|---|---|---|---|---|---|---|---|---|---|---|---|
| 177 | H | Cl | H | 237-240 | $C_{25}H_{18}Cl_2N_2O_3$ | 64.53 | 3.89 | 6.02 | 62.86 | 3.79 | 6.10[1] |
| 178 | H | CH₃ | H | 223-225 | $C_{26}H_{21}ClN_2O_3$ | 70.19 | 4.76 | 6.30 | 69.95 | 4.64 | 6.17 |
| 179 | H | OCH₃ | H | 226-228 | $C_{26}H_{21}ClN_2O_4$ | 67.75 | 4.59 | 6.08 | 67.64 | 4.51 | 6.05 |
| 180 | Cl | Cl | H | 214-217 | $C_{25}H_{17}Cl_3N_2O_3$ | 60.08 | 3.43 | 5.61 | 59.59 | 3.26 | 5.57 |
| 181 | H | Cl | Cl | 231-233 | $C_{25}H_{17}Cl_3N_2O_3$ | 60.08 | 3.43 | 5.61 | 59.97 | 3.30 | 5.62 |
| 182 | Cl | H | NO₂ | 181-184 | $C_{25}H_{17}Cl_2N_3O_5$ | 58.84 | 3.36 | 8.23 | 60.16 | 3.51 | 7.72[1] |

[1]Structure confirmed by spectral analysis.

Structure (Examples 183-190):

| Example | M | X | X¹ | X² | Y | Y¹ | R | R¹ | MP(°C.) | Molecular Formula | % C calc | % H calc | % N calc | % C found | % H found | % N found |
|---|---|---|---|---|---|---|---|---|---|---|---|---|---|---|---|---|
| 183 | N | Cl | H | H | Cl | H | Br | Br | 196 dec | $C_{23}H_{13}Br_2Cl_2N_2O_3$ | 45.28 | 2.15 | 6.89 | 44.67 | 2.01 | 7.69 |
| 184 | N | Cl | H | H | Cl | H | H | Br | 188 dec | $C_{23}H_{14}BrCl_2N_2O_3$ | 52.00 | 2.66 | 7.91 | 51.52 | 2.50 | 9.08 |

| Example | M | X | X¹ | X² | Y | Y¹ | Z | Z¹ | MP(°C.) | Molecular Formula | % C calc | % H calc | % N calc | % C found | % H found | % N found |
|---|---|---|---|---|---|---|---|---|---|---|---|---|---|---|---|---|
| 185 | CH | H | Cl | H | Cl | Cl | H | Br | 274 dec | $C_{24}H_{14}BrCl_3N_2O_3$ | 51.05 | 2.50 | 4.96 | 51.00 | 2.36 | 5.24 |
| 186 | CCl | H | Cl | H | Cl | Cl | H | Br | 290 dec | $C_{24}H_{13}BrCl_4N_2O_3$ | 48.12 | 2.19 | 4.68 | 48.15 | 2.09 | 4.75 |
| 187 | CH | Cl | H | NO₂ | Cl | Cl | H | Br | 256 dec | $C_{24}H_{13}BrCl_3N_3O_5$ | 47.28 | 2.15 | 6.89 | 47.22 | 2.03 | 6.86 |
| 188 | CH | H | CH₃ | H | Cl | Cl | H | Br | 291 dec | $C_{25}H_{17}BrCl_2N_2O_3$ | 55.17 | 3.15 | 5.15 | 55.27 | 3.02 | 5.16 |
| 189 | CH | H | OCH₃ | H | Cl | Cl | H | Br | 281 dec | $C_{25}H_{17}BrCl_2N_2O_4$ | 53.60 | 3.06 | 5.00 | 53.62 | 2.91 | 4.99 |
| 190 | CH | Cl | Cl | H | Cl | Cl | H | Br | 255 dec | $C_{24}H_{13}BrCl_4N_2O_3$ | 48.12 | 2.19 | 4.68 | 48.08 | 2.09 | 4.72 |

Structure (Examples 191-198):

| Example | M | X | X¹ | X² | Y | MP(°C.) | Molecular Formula | % C calc | % H calc | % N calc | % C found | % H found | % N found |
|---|---|---|---|---|---|---|---|---|---|---|---|---|---|
| 191 | N | Cl | H | H | H | 190 dec | $C_{23}H_{14}Cl_3N_3O_3$ | 56.75 | 2.90 | 8.63 | 56.62 | 3.20 | 8.87 |
| 192 | N | Cl | H | H | Cl | 224 dec | $C_{23}H_{13}Cl_4N_3O_3$ | 53.00 | 2.51 | 8.06 | 52.29 | 2.42 | 8.15 |
| 193 | CH | H | Cl | H | Cl | 262 dec | $C_{24}H_{14}Cl_4N_2O_3$ | 55.41 | 2.71 | 5.39 | 55.18 | 2.76 | 5.74 |
| 194 | CCl | H | Cl | H | Cl | 256 dec | $C_{24}H_{13}Cl_5N_2O_3$ | 51.97 | 2.36 | 5.05 | 51.80 | 2.77 | 4.72 |
| 195 | CH | Cl | H | NO₂ | Cl | 248 dec | $C_{24}H_{13}Cl_4N_3O_5$ | 51.00 | 2.32 | 7.44 | 53.66 | 2.73 | 7.16[1] |
| 196 | CH | H | CH₃ | H | Cl | 272 dec | $C_{25}H_{17}Cl_3N_2O_3$ | 60.08 | 3.43 | 5.61 | 61.51 | 3.67 | 5.64 |
| 197 | CH | H | OCH₃ | H | Cl | 265 dec | $C_{25}H_{17}Cl_3N_2O_4$ | 58.22 | 3.32 | 5.43 | 58.30 | 3.39 | 5.60 |
| 198 | CH | Cl | Cl | H | Cl | 248 dec | $C_{25}H_{13}Cl_5N_2O_3$ | 51.97 | 2.36 | 5.05 | 51.70 | 2.31 | 5.11 |

TABLE V

PHYSICAL PROPERTIES OF 1-(4-[1-NAPHTHOXY]PHENYL)-3-BENZOYLUREAS

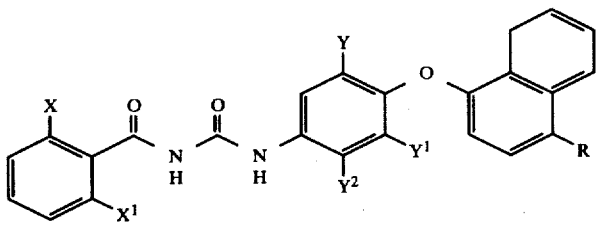

| | Structure | | | | | | Molecular | ELEMENTAL ANALYSIS | | | | | |
| | | | | | | | | CALCULATED | | | FOUND | | |
| Example | X | $X^1$ | Y | $Y^1$ | $Y^2$ | R | MP (°C.) | Formula | % C | % H | % N | % C | % H | % N |
|---|---|---|---|---|---|---|---|---|---|---|---|---|---|---|
| 199 | Cl | Cl | $CH_3$ | Cl | $CH_3$ | Cl | 229 dec | $C_{26}H_{18}Cl_4N_2O_3$ | 56.96 | 3.31 | 5.11 | 55.58 | 5.08 | 5.39 |
| 200 | Cl | H | $CH_3$ | Cl | $CH_3$ | Cl | 187 dec | $C_{26}H_{19}Cl_3N_2O_3$ | 60.77 | 3.73 | 5.45 | 61.53 | 3.95 | 5.36 |
| 201 | Cl | F | $CH_3$ | Cl | $CH_3$ | Cl | 235 dec | $C_{26}H_{18}Cl_3FN_2O_3$ | 58.72 | 3.41 | 5.27 | 59.25 | 3.40 | 5.32 |
| 202 | F | F | $CH_3$ | Cl | $CH_3$ | Cl | 187 dec | $C_{26}H_{18}Cl_2F_2N_2O_3$ | 60.59 | 3.52 | 5.44 | 59.95 | 3.28 | 6.19 |
| 203 | Cl | H | $CH_3$ | $CH_3$ | H | Cl | 226–229 | $C_{26}H_{20}Cl_2N_2O_3$ | 65.14 | 4.21 | 5.85 | 64.97 | 4.30 | 5.89 |

TABLE VI

PHYSICAL PROPERTIES OF 1-(4-[1-5,6,7,8-TETRAHYDRO-1-NAPTHTHOXY]PHENYL)-3-BENZOYLUREAS

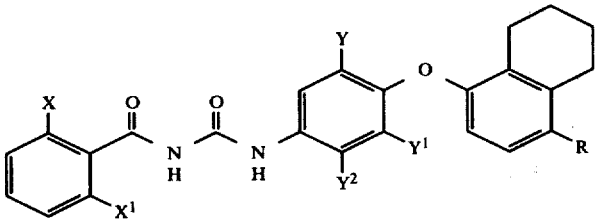

| | | | | | | | | Molecular | ELEMENTAL ANALYSIS | | | | | |
| | | | | | | | | | CALCULATED | | | FOUND | | |
| Example | X | $X^1$ | Y | $Y^1$ | $Y^2$ | R | MP (°C.) | Formula | % C | % H | % N | % C | % H | % N |
|---|---|---|---|---|---|---|---|---|---|---|---|---|---|---|
| 204 | Cl | Cl | $CH_3$ | Cl | $CH_3$ | $N(CH_3)_2$ | 288 dec | C5HClNO | 59.95 | 5.03 | 7.49 | 59.48 | 4.92 | 7.45 |
| 205 | Cl | F | $CH_3$ | Cl | $CH_3$ | $N(CH_3)_2$ | 208 dec | $C_{28}H_{28}Cl_2FN_3O_3$ | 61.77 | 5.18 | 7.72 | 62.58 | 5.21 | 7.47 |
| 206 | F | F | $CH_3$ | Cl | $CH_3$ | $N(CH_3)_2$ | 219 dec | $C_{28}H_{28}ClF_2N_3O_3$ | 63.69 | 5.37 | 7.96 | 63.71 | 5.31 | 7.83 |
| 207 | Cl | H | $CH_3$ | Cl | $CH_3$ | $N(CH_3)_2$ | 193 dec | $C_{28}H_{29}Cl_2N_3O_3$ | 63.88 | 5.55 | 7.98 | 62.37 | 5.38 | 7.80 |
| 208 | Cl | F | $CH_3$ | Cl | $CH_3$ | Cl | 236 dec | $C_{26}H_{22}ClFN_2O_3$ | 58.28 | 4.14 | 5.23 | 58.35 | 4.06 | 5.28 |
| 209 | F | F | $CH_3$ | Cl | $CH_3$ | Cl | 224–226 | $C_{26}H_{22}Cl_2F_2N_2O_3$ | 62.03 | 4.41 | 5.57 | 60.03 | 4.15 | 5.49 |
| 210 | Cl | H | $CH_3$ | Cl | $CH_3$ | Cl | 238 dec | $C_{26}H_{23}Cl_3N_2O_3$ | 60.30 | 4.48 | 5.41 | 60.48 | 4.50 | 5.40 |

Selected bicyclooxyphenyl ureas representative of those prepared in accordance with this invention and having the same utility were tested with respect to their insecticidal and miticidal activity.

Suspensions of the test compounds were prepared by dissolving one gram of compound in 50 milliliters of acetone in which had been dissolved 0.1 gram (10 percent of the weight of compound) of an alkylphenoxyethanol surfactant, as an emulsifying or dispersing agent. The resulting solution was mixed into 160 milliliters of water to give roughly 200 milliliters of a suspension containing the compound in finely divided form. The thus prepared stock suspension contained 0.5 percent by weight of compound. The test concentrations employed in the tests described hereinbelow were obtained by diluting the stock suspension with water. The test procedures were as follows:

Southern Armyworm

Larvae of the southern armyworm (SAW) (Spodopteraeridania, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for five days. Although the larvae could easily consume the whole leaf within twenty-four hours, no more food was added. Larvae which were unable to move the length of the body, even upon stimulation by prodding, were considered dead.

Mexican Bean Beetle

Fourth instar larvae of the Mexican bean beetle (MBB), (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5. for five days. Although the larvae could easily consume the leaf within 24 to 48 hours, no more food was added. Larvae which were unable to move the length of the body, even upon stimulation, were considered dead.

MITE FOILAGE SPRAY TEST

Adults and nymphal stages of the two-spotted mite (*Tetranychus urticae* Koch) reared on Tendergreen beans under controlled conditions (80±5° F. and 50±5 percent relative humidity). Infested leaves from the stock culture are placed on the primary leaves of 2 bean plants 6-8 inches in height. A sufficient number of mites for testing (150-200) will transfer from the excised leaves to the fresh plants.

Infested Tendergreen bean plants of standard height and age are placed on a revolving turntable. A formulated water mixture of the chemical (100 mL) is applied to the plants by use of a DeVilbiss spray gun with air pressure set at 40 pounds. Application of this volume of formulated compound takes 25 seconds. This volume of spray is sufficient to wet the plants to run-off.

The test compounds are formulated by a standard procedure of solution in acetone, addition of an emulsifier, and dilution with water. Primary spray applications are conducted at 500 ppm.

The treated plants are held at 80±5° F. and 50±5 percent relative humidity for a period of 7 days when mortality counts of motile forms (adults and nymphs) are made.

Microscopic examination of motile forms is made on one leaf from each of the 2 test plants. Any individual which is capable of locomotion upon stimulation is considered living.

MITE OVICIDE TEST

The egg of the two-spotted mite (*Tetranychus urticae* (Koch) obtained from adults reared on Tendergreen beans under controlled conditions (80±5° F. and 50±5 percent relative humidity). Heavily infested leaves from the stock culture are placed on uninfested bean plants. Females are allowed to oviposit for a period of 24 hours, and the leaves of the plants are then dipped in an 1000 ppm solution of TEPP in order to kill the motile forms and prevent additional egg laying. TEPP does not affect the viability of the eggs.

The plants are placed on a revolving turntable. A formulated water mixture of the chemical (100 mL) is applied to the plants by use of a DeVilbiss spray gun with air pressure set at 40 pounds. Application of this volume of formulated compound takes 25 seconds. This volume of spray is sufficient to wet the plants to runoff. An equivalent amount of a water solution containing acetone and emulsifier in the same concentrations as the insecticidal mixture but without the candidate insecticide is also sprayed on the infested plants as a check or control.

The test compounds are formulated by a standard procedure of solution in acetone, addition of an emulsifier, and dilution with water. Primary screening tests are conducted at 500 ppm.

The treated plants are held at 80±5° F. and 50±5 percent relative humidity for 7 days after which counts are made.

Microscopic examination is made of the plant leaves, and the number of unhatched eggs (considered dead) and empty egg shells (living eggs) are noted. The results obtained are set forth in tables VII-XI below:

TABLE VII

Insecticidal Activity of 1-(4-[1-Naphthoxy]phenyl)-3-Benzoylurea

| | Mortality Rating* | |
|---|---|---|
| Example | Southern Armyworm | Mexican Bean Beetle |
| 2 | A | A |
| 3 | C | C |
| 4 | A | A |
| 5 | A | A |
| 6 | C | C |
| 7 | C | C |
| 8 | A | A |
| 9 | A | A |
| 10 | A | A |
| 11 | A | A |
| 12 | A | A |
| 13 | A | A |
| 14 | A | A |
| 15 | A | A |
| 16 | A | A |
| 17 | A | A |
| 18 | A | B |
| 19 | A | A |
| 20 | A | C |
| 21 | A | A |
| 22 | A | A |
| 23 | A | A |
| 24 | B | C |
| 25 | A | A |
| 26 | C | C |
| 27 | A | A |
| 28 | A | A |
| 29 | A | C |
| 30 | A | A |
| 31 | C | B |
| 32 | A | A |
| 33 | A | A |
| 34 | A | A |
| 35 | A | A |
| 36 | A | A |
| 37 | A | A |
| 38 | A | A |
| 39 | A | A |
| 40 | A | A |
| 41 | A | A |
| 42 | A | A |
| 43 | A | A |
| 44 | A | B |
| 45 | A | A |
| 46 | C | C |
| 47 | A | A |
| 48 | A | A |
| 49 | A | A |
| 50 | C | C |

TABLE VII-continued

Insecticidal Activity of 1-(4-[1-Naphthoxy]phenyl)-3-Benzoylurea

| Example | Southern Armyworm | Mexican Bean Beetle |
|---|---|---|
| 51 | C | C |
| 52 | A | A |
| 53 | A | A |
| 54 | A | A |
| 55 | A | A |
| 56 | A | A |
| 57 | A | A |
| 58 | A | A |
| 59 | A | A |
| 60 | A | A |
| 61 | A | A |
| 62 | A | A |
| 63 | A | A |
| 64 | A | A |
| 65 | A | A |
| 66 | A | A |
| 67 | A | A |
| 68 | A | A |
| 69 | A | A |
| 70 | A | A |
| 71 | A | A |
| 72 | A | A |
| 73 | A | A |
| 74 | A | A |
| 75 | A | A |
| 76 | A | A |
| 77 | A | A |
| 78 | A | A |
| 79 | C | C |
| 80 | A | A |
| 81 | A | A |
| 82 | A | A |
| 170 | C | C |
| 171 | A | B |
| 172 | A | A |
| 173 | A | A |
| 174 | C | C |
| 178 | C | C |
| 179 | C | C |
| 180 | C | C |
| 181 | C | C |
| 182 | A | A |
| 191 | A | A |
| 192 | A | A |
| 193 | C | C |
| 194 | C | C |
| 195 | A | C |
| 196 | C | C |
| 197 | C | C |
| 198 | C | C |
| 83 | A | A |
| 84 | A | A |
| 85 | A | A |
| 86 | A | A |
| 87 | A | A |
| 88 | A | A |
| 89 | A | A |
| 90 | A | A |
| 199 | A | A |
| 200 | A | A |
| 201 | A | A |
| 202 | A | A |
| 203 | A | A |

*At 500 ppm.
A = 81–100% kill;
B = 31–80% kill;
C = 0–30% kill.

TABLE VIII

Insecticidal Activity Of 1-(4-[5,6,7,8-Tetrahydro-1-Naphthoxy]phenyl)-3-Benzoylureas

| Example | Southern Armyworm | Mexican Bean Beetle |
|---|---|---|
| 91 | A | A |
| 92 | A | A |
| 93 | A | A |
| 94 | B | A |
| 95 | A | A |
| 96 | A | A |
| 97 | A | A |
| 98 | A | A |
| 99 | A | A |
| 100 | A | A |
| 101 | A | A |
| 102 | A | A |
| 103 | A | A |
| 104 | A | A |
| 105 | A | A |
| 106 | A | A |
| 107 | C | B |
| 108 | A | A |
| 109 | A | A |
| 110 | A | A |
| 111 | A | A |
| 112 | A | A |
| 113 | A | A |
| 114 | A | A |
| 115 | A | A |
| 116 | A | A |
| 117 | A | A |
| 118 | A | A |
| 119 | A | A |
| 120 | A | A |
| 121 | A | A |
| 122 | A | A |
| 123 | A | A |
| 124 | A | A |
| 125 | A | A |
| 126 | A | A |
| 127 | A | A |
| 128 | A | A |
| 129 | A | A |
| 130 | A | A |
| 131 | A | A |
| 132 | A | A |
| 133 | A | A |
| 134 | A | A |
| 135 | A | A |
| 136 | A | A |
| 137 | A | A |
| 138 | A | A |
| 139 | A | A |
| 204 | A | A |
| 205 | A | A |

*at 500 ppm.
A = 81–100% kill;
B = 31–80% kill;
C = 0–30% kill.

TABLE IX

Insecticidal Activity Of 1-(4-[2-Naphthoxy]phenyl)-3-Benzoylurea

| Example | Southern Armyworm | Mexican Bean Beetle |
|---|---|---|
| 206 | A | A |
| 207 | A | A |
| 208 | A | A |
| 209 | A | A |
| 210 | A | A |
| 140 | A | A |
| 141 | A | A |
| 142 | A | A |
| 143 | A | C |
| 144 | A | A |
| 145 | A | A |
| 146 | A | C |

TABLE IX-continued

Insecticidal Activity Of 1-(4-[2-Naphthoxy]-phenyl)-3-Benzoylurea

| | Mortality Rating* | |
|---|---|---|
| Example | Southern Armyworm | Mexican Bean Beetle |
| 147 | A | A |
| 148 | A | C |
| 149 | A | C |
| 150 | A | C |
| 151 | A | A |
| 152 | A | A |
| 153 | A | C |
| 154 | A | A |
| 155 | C | C |
| 156 | C | C |
| 157 | C | A |
| 158 | C | C |
| 159 | C | B |
| 160 | B | A |
| 183 | A | B |
| 184 | A | A |
| 185 | C | C |
| 186 | C | C |
| 159 | C | B |
| 160 | B | A |
| 183 | A | B |
| 184 | A | A |
| 185 | C | C |
| 186 | C | C |
| 187 | A | C |
| 188 | C | C |
| 189 | C | C |
| 190 | C | C |

*At 500 ppm. A = 81–100% kill; B = 31–80% kill; C = 0–30% kill.

TABLE X

Insecticidal Activity Of 1-(4-Bicyclooxyphenyl)-3-Benzoylureas

| | Mortality Rating* | |
|---|---|---|
| Example | Southern Armyworm | Mexican Bean Beetle |
| 161 | A | C |
| 162 | A | A |
| 163 | A | A |
| 164 | A | A |
| 165 | B | A |
| 166 | A | A |
| 167 | A | A |
| 168 | C | B |
| 169 | A | A |
| 174 | A | A |
| 175 | A | A |
| 176 | A | A |

*At 500 ppm. A = 81–100% kill; B = 31–80% kill; C = 0–30% kill.

TABLE XI

Toxicity of 1-(4-Bicyclooxyphenyl)-3-Benzoyl ureas Against Two-Spotted Mites

| | Mortality Rating* | | |
|---|---|---|---|
| Example | Adults | Larvae | Eggs |
| 39 | B | A | A |
| 62 | C | A | A |
| 63 | C | A | A |
| 73 | C | A | A |
| 74 | C | A | A |
| 75 | C | A | A |
| 81 | C | A | A |
| 82 | C | A | B |
| 103 | C | A | A |
| 110 | A | A | A |
| 111 | C | A | B |
| 114 | C | — | A |
| | C | A | A |
| 116 | C | — | B |
| 117 | C | — | A |
| 121 | C | — | A |
| 122 | B | A | B |
| 124 | B | A | C |
| 125 | A | A | C |
| 130 | C | — | A |
| 152 | B | C | C |
| 202 | C | — | A |
| 204 | C | — | A |
| 207 | C | — | A |

*At 500 ppm. A = 81–100% kill; B = 31–80% kill; C = 0–30% kill.

In order to demonstrate the insecticidal properties of benzoyl ureas of this invention, a comparison of activity was made with a known benzoyl urea insecticide produced by Phillips Duphar of the Netherlands. The following examples set forth in Table XII demonstrate the superiority of the compositions of this invention over the known insecticide.

TABLE XII

| Composition | Conc. (ppm) | Mexican Bean Beetle % Mortality After 5 Days |
|---|---|---|
| 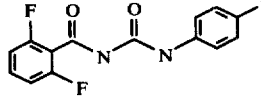 | 8 | 60 |
| (Known Compound DIMILIN) | | |
| EXAMPLE 2 | 8 | 100 |
| EXAMPLE 17 | 8 | 100 |
| EXAMPLE 39 | 8 | 100 |
| EXAMPLE 63 | 8 | 100 |
| EXAMPLE 97 | 8 | 100 |
| EXAMPLE 114 | 8 | 100 |
| EXAMPLE 117 | 8 | 100 |
| EXAMPLE 200 | 8 | 100 |
| EXAMPLE 202 | 8 | 100 |
| EXAMPLE 203 | 8 | 100 |

Although the invention has been illustrated by the preceding examples, it is not to be construed as being limited to the materials employed therein, but rather, the invention encompasses the generic area as hereinbefore disclosed. Various modifications and embodiments can be made without departing from the spirit and scope thereof.

What is claimed is:

1. A composition of the formula:

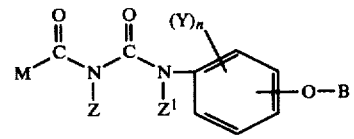

wherein M represents a monocyclic aromatic ring system or a monocyclic heterocyclic ring system containing up to 2 nitrogen atoms, and wherein the ring can contain up to four X substituents wherein each X individually can be halogen, nitro, cyano, or alkyl, polyhaloalkyl, alkoxy or polyhaloalkoxy of from 1 to 3 carbon atoms;

Z and $Z^1$ individually are hydrogen or alkyl of from 1 to 8 carbon atoms, or alkyl of from 1 to 8 carbon atoms which is substituted with at least one of halogen, hydroxyl or alkoxy;

Y individually represents halogen, or alkyl, polyhaloalkyl, alkoxy or polyhaloalkoxy of from 1 to 3 carbon atoms, and n has a value of from 0 to 4;

B is a bicyclic fused ring system which is attached to the oxygen through a carbocyclic ring and wherein (a) at least one ring is a six-membered, unsaturated carbocyclic ring which can contain up to two R and $R^1$ substituents wherein R and $R^1$ can be halogen, nitro, cyano, amino, formamido, formamidino, phenylsulfenyl, phenylsulfinyl, phenylsulfonyl, phenylsulfamido wherein the phenyl ring optionally may be substituted with one or more halogen, nitro, or alkyl, polyhaloalkyl, alkoxy or polyhaloalkoxy of from 1 to 3 carbon atoms, or R and $R^1$ individually are alkyl, alkoxy, polyhaloalkyl, polyhaloalkoxy, alkenyloxy, polyhaloalkenyloxy, alkynyloxy, polyhaloalkynyloxy, alkylsulfenyl, poyhaloalkylsulfenyl, alkylsulfinyl, polyhaloalkylsulfinyl, alkylsulfonyl, polyhaloalkylsulfonyl, mono- or di-alkylsulfamido, mono- or di-alkylamino, alkylcarbonylamino, alkoxycarbonylamino, mono- or di-alkylaminocarbonyloxy of up to 6 carbon atoms, and (b) the second ring, hereinafter also referred to as A, when it is not a five or six-membered carbocyclic can be a five or six-membered saturated or unsaturated heterocyclic ring which can contain in any combination carbonyl or one or two oxygen or sulfur, and up to two $R^2$ and $R^3$ substituents attached to unsaturated ring carbon atoms wherein $R^2$ and $R^3$ individually can be halogen, nitro, cyano, or alkyl, polyhaloalkyl, alkoxy, polyhaloalkoxy, alkylthio, arylthio, alkylsulfinyl, arylsulfinyl, alkylsulfonyl, arylsulfonyl, alkylsulfamido, arylsulfamido, alkoxycarbonylamino, or alkylcarbonylamino of from 1 to 6 carbon atoms, or can contain up to two $R^4$ and $R^5$ substituents attached to saturated carbon atoms of the chain wherein $R^4$ and $R^5$ individually can be alkyl or polyhaloalkyl of from 1 to 6 carbon atoms; with the proviso that when B is a naphthyl group it is attached through an oxygen to the number 4 carbon atom of the phenyl group, and with the further proviso that (a) if X is halogen and is mono or disubstituted in the ortho position of a benzoyl ring (b) if Z and $Z^1$, are hydrogen (c) if no more than 2 of R, $R^1$, $R^2$ or $R^3$ are hydrogen, chloro or bromo, and (d) if Y represents chloro, then n has a value of at least 2.

2. A composition of the formula:

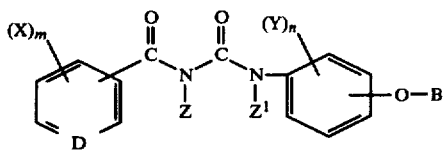

wherein D is nitrogen or carbon, m has a value of from zero to four and X, n, Z, $Z^1$, Y and B are as defined in claim 1.

3. A composition of the formula:

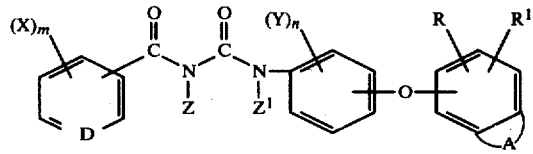

wherein D is nitrogen or carbon, X, n, Z, $Z^1$, Y, m, R, $R^1$ and A are as defined in claim 1.

4. The composition of the formula of claim 3 wherein the moiety:

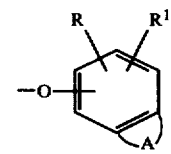

is selected from the group of

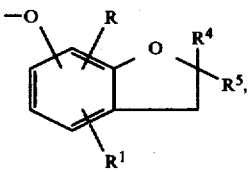

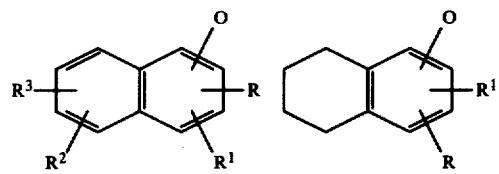

wherein R, $R^1$, $R^2$, $R^3$, $R^4$ and $R^5$ are as defined in claim 1.

5. A composition of the formula:

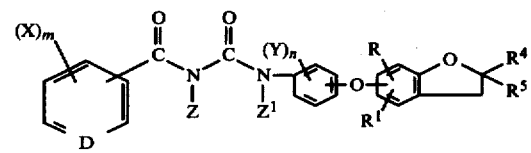

wherein X, D, n, m, Z, $Z^1$, Y, R, $R^1$, $R^4$ and $R^5$ are as defined in claim 2.

6. A composition of the formula:

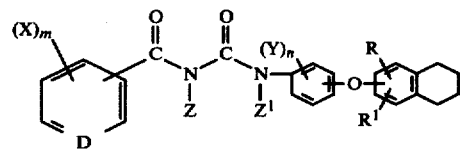

wherein X, D, n, m, Z, $Z^1$, Y, R and $R^1$ are as defined in claim 2.

7. A composition of the formula:

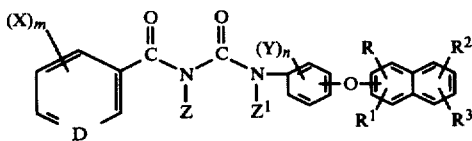

wherein X, D, n, m, Z, Z¹, Y, R, R¹, R² and R³ are as defined in claim 2.

8. A composition of the formula:

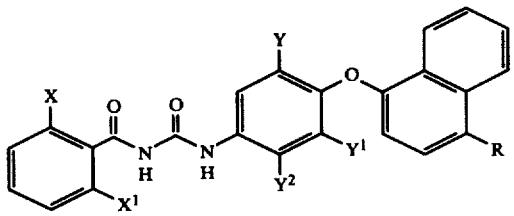

wherein R is chloro, alkoxy or dialkylamino of from 1 to 6 carbon atoms, X is chloro or fluoro, X¹ is hydrogen, chloro or fluoro, Y is hydrogen, chloro, bromo, methyl or methoxy, Y¹ and Y² independently are hydrogen, chloro, bromo or methyl with the proviso that if Y¹ and Y² are hydrogen and if R is chloro then Y can not be hydrogen or chloro.

9. A composition of the formula:

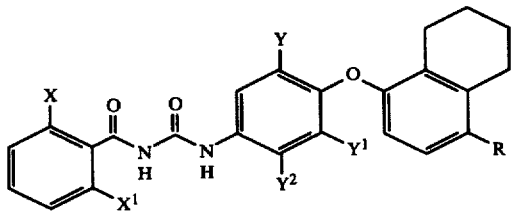

wherein R is chloro, or dialkylamine of 1 to 6 carbon atoms, X is hydrogen, chloro or fluoro, X¹ is chloro or fluoro, Y is hydrogen chloro, bromo, methyl or methoxy, Y¹ and Y² independently are hydrogen, chloro, bromo or methyl.

10. A composition of the formula:

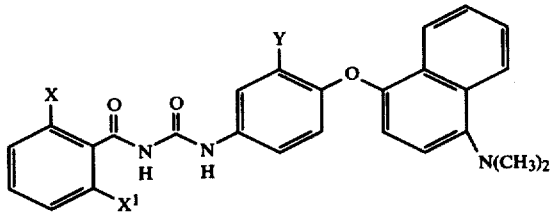

wherein X is chloro or fluoro, X¹ is hydrogen, chloro or fluoro and Y is hydrogen or chloro.

11. A composition of the formula:

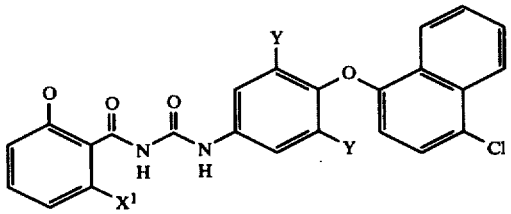

wherein X is chloro or fluoro, X¹ is hydrogen, chloro or fluoro, Y is chloro, bromo or methyl.

12. A composition of the formula:

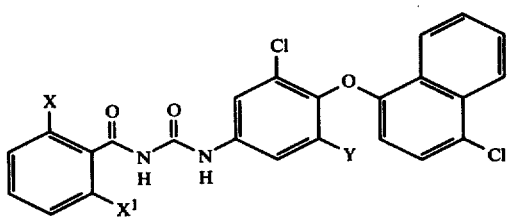

wherein X is chloro or fluoro, X¹ is hydrogen, chloro or fluoro and Y is chloro or methyl.

13. A composition of the formula:

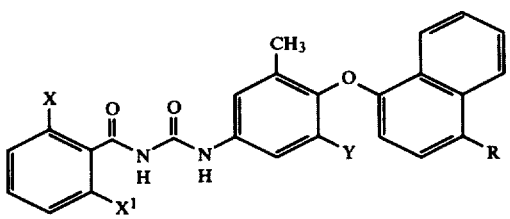

wherein X is chloro or fluoro, X¹ is hydrogen, chloro or fluoro and R is chloro or methoxy.

14. A composition of the formula:

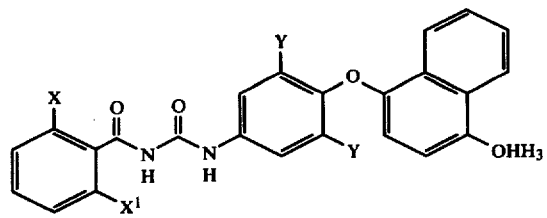

wherein X is chloro or fluoro, X¹ is hydrogen, chloro or fluoro and Y is chloro or methyl.

15. A composition of the formula:

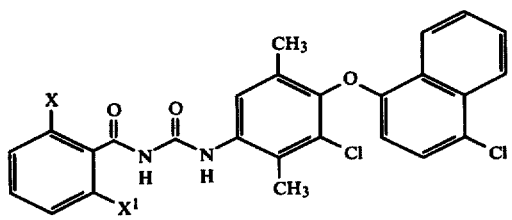

wherein X is chloro or fluoro and $X^1$ is hydrogen, chloro or fluoro.

16. A composition of the formula:

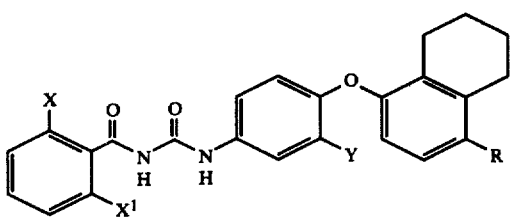

wherein X is chloro or fluoro, $X^1$ is hydrogen, chloro or fluoro, Y is chloro, methyl or methoxy, and R is chloro or dimethylamino.

17. A composition of the formula:

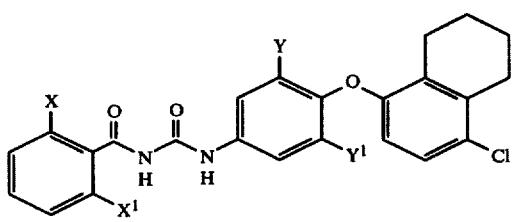

wherein X is chloro or fluoro, $X^1$ is hydrogen, chloro or fluoro, Y and $Y^1$ are chloro, bromo or methyl or a combination of chloro and methyl.

18. A composition of the formula:

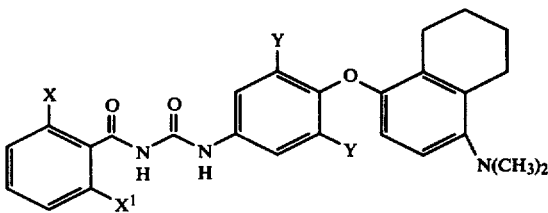

wherein X is chloro or fluoro, $X^1$ is hydrogen, chlor or fluoro and Y is chloro or methyl.

19. A composition of the formula:

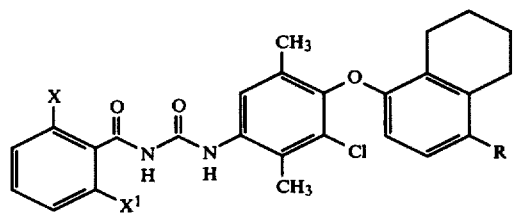

wherein X is chloro or fluoro, $X^1$ is hydrogen, chloro or fluoro and R is chloro or dimethylamino.

20. The composition of claim 7 which is 1-(4-[4-chloro-1-naphthoxy]-3,5-dichloro phenyl)-3-(2,6-difluoro benzoyl)urea.

21. The composition of claim 7 which is 1-(4-[4-chloro-1-naphthoxy]-3,5-dichlorophenyl)-3-(2-chloro benzoyl) urea.

22. The composition of claim 7 which is 1-(4-[4-chloro-1-naphthoxy]-3-methyl phenyl)-3-(2-chlorobenzoyl) urea.

23. The composition of claim 7 which is 1-(4-[4-chloro-1-naphthoxy]-3-methylphenyl)-3-(2-chloro-6-fluoro benzoyl) urea.

24. The composition of claim 7 which is 1-(3,5-dichloro-4-[4-methoxy-1-naphthoxy]phenyl)-3-(2,6-difluoro benzoyl) urea.

25. The composition of claim 7 which is 1-(3,5-dichloro-4-[4-methoxy-1-naphthoxy]phenyl)-3-(2-chlorobenzoyl) urea.

26. The composition of claim 7 which is 1-(4-[4-chloro-1-naphthoxy]-3,5-dichlorophenyl)-3-(2-fluorobenzoyl) urea.

27. The composition of claim 7 which is 1-(4-[4-chloro-1-naphthoxy]-3,5-dimethyl phenyl)-3-(2-chloro benzoyl) urea.

28. The composition of claim 7 which is 1-(4-[4-chloro-1-naphthoxy]-3,5-dimethyl phenyl)-3-(2,6-difluoro benzoyl) urea.

29. The composition of claim 7 which is 1-(4-[4-chloro-1-naphthoxy]-3,5-dimethyl phenyl)-3-(2-fluoro benzoyl) urea.

30. The composition of claim 7 which is 1-(3-chloro-4-[4-chloro-1-naphthoxy]-2,5-dimethylphenyl)-3-(2,6-difluoro benzoyl) urea.

31. The composition of claim 7 which is 1-(3-chloro-4-[4-chloro-1-naphthoxy]-2,5-dimethyl-phenyl)-3-(2-chloro benzoyl) urea.

32. The composition of claim 6 which is 1-(4-[4-chloro-5,6,7,8-tetrahydro-1-naphthoxy]-3,5-dimethyl phenyl)-3-(2-chloro benzoyl) urea.

33. The composition of claim 6 which is 1-(4-[4-chloro-5,6,7,8-tetrahydro-1-naphthoxy]-3,5-dimethyl phenyl)-3-(2,6-difluoro benzoyl) urea.

34. The composition of claim 6 which is 1-(4-[4-chloro-5,6,7,8-tetrahydro-1-naphthoxy]-2,5-dimethyl phenyl)-3-(2-chloro benzoyl) urea.

35. The composition of claim 6 which is 1-(3-chloro-4-[4-chloro-5,6,7,8-tetrahydro-1-naphthoxy]-2,5-dimethyl phenyl)-3-(2,6-difluoro benzoyl) urea.

36. The composition of the claim 6 which is 1-(3-chloro-4-[4-chloro-5,6,7,8-tetrahydro-1-naphthoxy]-2,5-dimethyl phenyl)-3-(2-chloro benzoyl)-urea.

37. An insecticidal or acaricidal pesticide composition comprising an acceptable carrier and a pesticidally effective amount of the composition of claim 1.

38. An insecticidal or acaricidal pesticide composition comprising an acceptable carrier and a pesticidally effective amount of the composition of claim 2.

39. An insecticidal or acaricidal pesticide composition comprising an acceptable carrier and a pesticidally effective amount of the composition of claim 3.

40. An insecticidal or acaricidal pesticide composition comprising an acceptable carrier and a pesticidally effective amount of the composition of claim 4.

41. An insecticidal or acaricidal pesticide composition comprising an acceptable carrier and a pesticidally effective amount of the composition of claim 5.

42. An insecticidal or acaricidal pesticide composition comprising an acceptable carrier and a pesticidally effective amount of the composition of claim 6.

43. An insecticidal or acaricidal pesticide composition comprising an acceptable carrier and a pesticidally effective amount of the composition of claim 7.

44. An insecticidal or acaricidal pesticide composition comprising an acceptable carrier and a pesticidally effective amount of the composition of claim 8.

45. An insecticidal or acaricidal pesticide composition comprising an acceptable carrier and a pesticidally effective amount of the composition of claim 9.

46. An insecticidal or acaricidal pesticide composition comprising an acceptable carrier and an insecticidally effective amount of the composition of claim 10.

47. An insecticidal or acaricidal pesticide composition comprising an acceptable carrier and a pesticidally effective amount of the composition of claim 11.

48. An insecticidal or acaricidal pesticide composition comprising an acceptable carrier and a pesticidally effective amount of the composition of claim 12.

49. An insecticidal or acaricidal pesticide composition comprising an acceptable carrier and a pesticidally effective amount of the composition of claim 13.

50. An insecticidal or acarical pesticide composition comprising an acceptable carrier and a pesticidally effective amount of the composition of claim 14.

51. An insecticidal or acaricidal pesticide composition comprising an acceptable carrier and a pesticidally effective amount of the composition of claim 15.

52. An insecticidal or acaricidal pesticide composition comprising an acceptable carrier and a pesticidally effective amount of the composition of claim 16.

53. An insectidial or acarical pesticide composition comprising an acceptable carrier and a pesticidally effective amount of the composition of claim 17.

54. An insecticidal or acarical pesticide composition comprising an acceptable carrier and a pesticidally effective amount of the composition of claim 18.

55. An insecticidal or acaricidal pesticide composition comprising an acceptable carrier and a pesticidally effective amount of the composition of claim 19.

56. An insecticidal or acaricidal pesticide composition comprising an acceptable carrier and a pesticidally effective amount of the composition of claim 20.

57. An insecticidal or acaricidal pesticide composition comprising an acceptable carrier and an insecticidally effective amount of the composition of claim 21.

58. An insecticidal or acaricidal pesticide composition comprising an acceptable carrier and a pesticidally effective amount of the composition of claim 22.

59. An insecticidal or acaricidal pesticide composition comprising an acceptable carrier and a pesticidally effective amount of the composition of claim 23.

60. An insecticidal or acaricidal pesticide composition comprising an acceptable carrier and a pesticidally effective amount of the composition of claim 25.

61. An insecticidal or acaricidal pesticide composition comprising an acceptable carrier and a pesticidally effective amount of the composition of claim 26.

62. An insecticidal or acaricidal pesticide composition comprising an acceptable carrier and a pesticidally effective amount of the composition of claim 31.

63. An insecticidal or acaricidal pesticide composition comprising an acceptable carrier and a pesticidally effective amount of the composition of claim 32.

64. An insecticidal or acaricidal pesticide composition comprising an acceptable carrier and a pesticidally effective amount of the composition of claim 34.

65. An insecticidal or acaricidal pesticide composition comprising an acceptable carrier and a pesticidally effective amount of the composition of claim 35.

66. A method of controlling insects and acarides which comprises subjecting said insects to a lethal amount of the composition of claim 1.

67. A method of controlling insects and acarides which comprises subjecting said insects to a lethal amount of the composition of claim 2.

68. A method of controlling insects and acarides which comprises subjecting said insects to a lethal amount of the composition of claim 3.

69. A method of controlling insects and acarides which comprises subjecting said insects to a lethal amount of the composition of claim 4.

70. A method of controlling insects and acarides which comprises subjecting said insects to a lethal amount of the composition of claim 5.

71. A method of controlling insects and acarides which comprises subjecting said insects to a lethal amount of the composition of claim 6.

72. A method of controling insects and acarides which comprises subjecting said insects to a lethal amount of the composition of claim 7.

73. A method of controlling insects and acarides which comprises subjecting said insects to a lethal amount of the composition of claim 8.

74. A method of controlling insects and acarides which comprises subjecting said insects to a lethal amount of the composition of claim 9.

75. A method of controlling insects and acarides which comprises subjecting said insects to a lethal amount of the composition of claim 10.

76. A method of controlling insects and acarides which comprises subjecting said insects to a lethal amount of the composition of claim 11.

77. A method of controlling insects and acarides which comprises subjecting said insects to a lethal amount of the composition of claim 12.

78. A method of controlling insects and acarides whch comprises subjecting said insects to a lethal amount of the composition of claim 13.

79. A method of controlling insects and acarides which comprises subjecting said insects to a lethal amount of the composition of claim 14.

80. A method of controlling insects and acarides which comprises subjecting said insects to a lethal amount of the composition of claim 15.

81. A method of controlling insects and acarides which comprises subjecting said insects to a lethal amount of the composition of claim 16.

82. A method of controlling insects and acarides which comprises subjecting said insects to a lethal amount of the composition of claim 17.

83. A method of controlling insects and acarides which comprises subjecting said insects to a lethal amount of the composition of claim 18.

84. A method of controlling insects and acarides which comprises subjecting said insects to a lethal amount of the composition of claim 19.

* * * * *